(12) United States Patent
Wu et al.

(10) Patent No.: US 10,307,041 B2
(45) Date of Patent: Jun. 4, 2019

(54) LENS COVER MODIFICATION

(71) Applicant: Medeon Biodesign, Inc., Taipei (TW)

(72) Inventors: I-Ching Wu, Los Altos, CA (US);
Thomas Hsu, Los Altos, CA (US);
Senzen Hsu, Los Altos, CA (US); John Stiggelbout, Los Altos, CA (US);
Torrey Smith, Los Altos, CA (US);
Hungwen Wei, Los Altos, CA (US);
Mengjhe Sie, Los Altos, CA (US)

(73) Assignee: Medeon Biodesign, Inc., Taipei (TW)

( * ) Notice: Subject to any disclaimer, the term of this patent is extended or adjusted under 35 U.S.C. 154(b) by 919 days.

(21) Appl. No.: 14/577,172

(22) Filed: Dec. 19, 2014

(65) Prior Publication Data

US 2015/0196194 A1      Jul. 16, 2015

Related U.S. Application Data

(63) Continuation-in-part of application No. 12/663,573, filed as application No. PCT/US2008/006923 on May 31, 2008, now Pat. No. 8,979,738.

(60) Provisional application No. 61/918,855, filed on Dec. 20, 2013, provisional application No. 60/933,693, filed on Jun. 8, 2007.

(51) Int. Cl.
*A61B 1/00* (2006.01)
*A61B 1/12* (2006.01)
*G02B 27/00* (2006.01)

(52) U.S. Cl.
CPC ...... *A61B 1/00135* (2013.01); *A61B 1/00089* (2013.01); *A61B 1/00101* (2013.01); *A61B 1/00142* (2013.01); *A61B 1/126* (2013.01); *G02B 27/0006* (2013.01)

(58) Field of Classification Search
CPC ............ A61B 1/00089; A61B 1/00135; A61B 1/00142
USPC ......... 600/121–125, 133, 157, 169, 175–176
See application file for complete search history.

(56) References Cited

U.S. PATENT DOCUMENTS

| 3,145,249 A | 8/1964 | Meltzer |
| 3,258,025 A | 6/1966 | Swallert |
| 4,524,920 A | 6/1985 | Kidawara et al. |

(Continued)

FOREIGN PATENT DOCUMENTS

| CN | 102711583 A | 10/2012 |
| CN | 103027660 A | 4/2013 |

(Continued)

OTHER PUBLICATIONS

Office Action in corresponding Chinese Patent Application 201480076020.5, dated Jun. 28, 2017, 10 pages.

(Continued)

*Primary Examiner* — Matthew J Kasztejna
(74) *Attorney, Agent, or Firm* — Dergosits & Noah LLP; Todd A. Noah

(57) ABSTRACT

The invention encompasses devices and methods used to keep the objective lens of a viewing or illuminating device, specifically an endoscope, free from obstructive fluid and dirt; specifically a device having a hollow body designed to fit over an endoscope, a transparent lens cover film that is retained within the device and that is threaded in front of the objective lens of an endoscope, thereby maintaining a clear and unobstructed transparent window in front of the endoscope lens, and an endcap configured to engage opposing edges of the lens cover film in a sealing manner.

8 Claims, 18 Drawing Sheets

(56) References Cited

U.S. PATENT DOCUMENTS

| | | |
|---|---|---|
| 5,167,220 A | 12/1992 | Brown |
| 5,207,213 A | 5/1993 | Auhll et al. |
| 5,225,001 A | 7/1993 | Manni et al. |
| 5,339,800 A | 8/1994 | Wilta et al. |
| 5,363,843 A | 11/1994 | Daneshvar |
| 5,392,766 A | 2/1995 | Masterson et al. |
| 5,400,767 A | 3/1995 | Murdoch |
| 5,464,008 A | 11/1995 | Kim |
| 5,469,841 A | 11/1995 | Kobayashi et al. |
| 5,514,084 A | 5/1996 | Fisher |
| 5,549,543 A | 8/1996 | Kim |
| 5,575,756 A | 11/1996 | Karasawa et al. |
| 5,830,127 A | 11/1998 | DeCastro |
| 6,017,333 A | 1/2000 | Bailey |
| 6,354,992 B1 | 3/2002 | Kato |
| 6,447,444 B1 | 9/2002 | Avni et al. |
| 6,447,446 B1 | 9/2002 | Smith et al. |
| 6,712,479 B1 | 3/2004 | Seitzinger et al. |
| 6,755,782 B2 | 6/2004 | Ogawa |
| 6,923,759 B2 | 8/2005 | Kasahara et al. |
| 8,088,065 B2 | 1/2012 | Karasawa et al. |
| 2003/0109837 A1 | 6/2003 | McBride-Sakai |
| 2006/0020165 A1 | 1/2006 | Adams |
| 2007/0049794 A1 | 3/2007 | Glassenberg et al. |
| 2008/0081948 A1 | 4/2008 | Weisenburgh et al. |
| 2010/0174144 A1 | 7/2010 | Hsu et al. |
| 2011/0082336 A1 | 4/2011 | Ito |
| 2012/0178995 A1 | 7/2012 | Newton, IV |
| 2012/0238818 A1 | 9/2012 | O'Prey et al. |

FOREIGN PATENT DOCUMENTS

| | | |
|---|---|---|
| EP | 0648044 | 10/1997 |
| EP | 1153567 | 11/2001 |
| EP | 2486845 A2 | 8/2012 |
| GB | 2188746 | 10/1987 |
| JP | S5263985 U | 5/1977 |
| JP | 61069019 | 4/1986 |
| JP | 08308789 A | 11/1996 |
| JP | 2005052229 | 3/2005 |
| JP | 2007105314 | 4/2007 |
| WO | 9220274 | 11/1992 |
| WO | 9532012 | 11/1995 |
| WO | 2008153841 | 12/2008 |

OTHER PUBLICATIONS

Search Report in corresponding European Patent Application 14878236.0, dated Sep. 6, 2017, 6 pages.

Communication from the European Patent Office dated Oct. 8, 2013 in corresponding European Patent Application No. 08768019.5.

Supplementary European Search Report dated Feb. 6, 2013 in corresponding European Patent Application No. EP08768019.

Written Opinion in related PCT Application No. PCT/US08/06923 dated Dec. 1, 2008.

Examination Report in Corresponding Canadian Application No. 2,937,148, dated Jul. 18, 2017, pp. 1-4.

a                              b

LENS COVER MODIFICATION

RELATED APPLICATIONS

This application is a continuation-in-part, claiming benefit of and priority to the related applications U.S. Provisional Patent Application No. 61/918,855, filed Dec. 20, 2013, and U.S. patent application Ser. No. 12/663,573, filed Dec. 8, 2009, which in claims benefit of and priority to PCT/US08/06923, filed May 31, 2008, and U.S. Provisional Patent Application No. 60/933,693, filed Jun. 8, 2007.

FIELD OF THE PRESENT DISCLOSURE

The invention relates to devices that keep the objective lens of a viewing or illuminating device, specifically an endoscope clear of debris while in use without the need for removing the endoscope from the body of the patient. In addition, a variation of the invention prevents direct contact of the endoscope surface and body tissue surface, thereby eliminating the need for sterilization of the endoscope.

BACKGROUND

Certain medical procedures require the insertion of a viewing device, an "endoscope", into a body cavity in order to view features and structures within the body cavity. Such an endoscope may be, for example, a gastroscope, pharyngoscope, laryngoscope, laparoscope, colonoscope or any other type of medical telescope. For the purpose of this disclosure, we shall use the term "endoscope" to include any viewing device that is inserted into the body of a subject and used to view internal structures. The endoscope may be rigid or flexible. Rigid endoscopes, such as standard laparoscopes, usually consist of a shaft of approximately 300-500 mm length, with an outer diameter of 5 mm to 12 mm, having an objective lens at one end and an eyepiece at the other end. In some instances, such as with fiber-optic gastroscopes, the device may be over a meter in length and may permit flexion and manipulation by the operator of the distal end. The shaft of the endoscope often contains light-transmitting fiber-optic bundles and/or lenses that transmit visual signals and light.

The endoscope also normally has a connection, adjacent to the eyepiece, for the attachment of an external light source which provides illumination, via light-transmitting fibers within the endoscope.

Prior to the introduction of a rigid endoscope, such as a laparoscope, the body cavity is generally inflated with a gas, usually carbon dioxide, using a gas insufflator.

Subsequently a plastic or metal sleeve or sheath, often referred to as a trocar, is inserted through the wall of the cavity. These sleeves contain a means of making a seal to prevent the leakage of gas from within the body cavity. The end of the endoscope containing the objective lens is inserted into the body cavity through the sleeve, the attached light-source activated and the features within the body cavity viewed through the eyepiece of the endoscope or on a video monitor receiving signals from a video camera attached to the eyepiece.

The objective lens of the endoscope often becomes soiled during operative procedure. Tissue particles, blood, mucous and other body fluids attach to the lens and obscure vision. The usual routine when such problem arises is to remove the endoscope from the patient's body and soak its distal end (the lens) in sterile water, wipe the lens with a sterile towel, and reinsert the laparoscope into the patient's body through the existing laparoscopic trocar. During some operative procedures, the endoscope may have to be removed frequently to have the lens wiped clean.

The loss of vision due to soiling of the objective lens of the endoscope can be a serious problem, especially if it occurs at a critical moment during surgery. It increases the time required for a procedure and necessitates repeated withdrawal and insertion of the endoscope which may produce trauma to the tissues. The covering of the objective lens of the endoscope by blood is often referred to as the "red video" sign. This is particularly serious if the bleeding is extensive and if time is wasted in removing, cleaning, and reinserting the lens. If clean, unobstructed lens is not available quickly enough for identification and control of the bleeding source, the procedure is more likely to be converted to an emergency "open" operative procedure requiring large surgical incisions.

A number of solutions have been developed for keeping the objective lens free of soiling. These include the use of water jets, ultrasound devices, liquid irrigation, and brushes (see U.S. Pat. Nos. 5,207,213, 5,549,543, 5,225,001, 5,167,220, 5,400,767, 5,514,084, 5,575,756, 5,830,127, 6,017,333, 6,354,992, 6,447,446, and patent publications US23109837A1, WO09220274A1, WO09532012A1). There are also several devices that solve the problem of fogging of the objective lens (see U.S. Pat. Nos. 5,549,543, 5,464,008, 6,712,479, and patent publication EP01153567A1). None of these describe or suggest the present invention.

There is clearly a long-felt need for devices and methods that maintain a clear and unobstructed view through the objective lens of an endoscope while in use; devices that clear obstructive fluids and debris from the optical/visual path of an endoscope while in use; and devices that eliminate the need for the endoscope to be withdrawn from the patient in order that the objective lens may be cleaned. There is a need for such devices that are simple and inexpensive to manufacture, that are simple to use and robust in use, and that can be used with a variety of endoscopic devices. The present invention provides such devices and methods of using them.

General Description

The invention encompasses devices and methods used to keep the objective lens of an endoscope, for example a laparoscope, free from debris, fluid and dirt.

The device can work equally with any type of viewing apparatus or illuminating apparatus to maintain a clear and unobstructed optical path.

In certain embodiments, the body of the device is a hollow tube or sheath designed to receive an endoscope within its lumen. The device is designed such that, in use, the distal end of the endoscope, having the objective lens theredisposed, is positioned within the lumen of the device at or near the distal tip of the body of the device.

Certain embodiments include a lens cover film wound onto a spool. For example, a flexible lens cover film may be rolled onto a first spool and systematically unrolled such that it passes in front of the objective lens of the endoscope. The lens cover film can be unrolled as needed to provide a clean and clear lens cover in front of the objective lens. The leading end of the lens cover film may be captured and wound onto on a second spool. By winding the lens cover film onto the second spool, the lens cover film is pulled from the first spool, along a pre-set travel path, passing in front of the objective lens, and wound onto the second spool. The travel path may be defined by guides of various design sufficient to hold and guide the lens cover film along the pre-set travel path. The guide may include rails or slits through which the lens cover film passes. The guide is generally constructed as an integral part of the body of the device. The guide may be supported with additional frames, scaffolds, or other device tip designs to provide a flat surface to the portion of the film in front of the lens. The guide and body of the device are further described in the detailed description.

The device may have additional frames, scaffolds, or specific distal tip design to allow the surface of lens cover film to become parallel to the surface of the objective lens at the distal end of the endoscope.

The device of the invention may optionally be incorporated into the structure of a viewing device such as an endoscope so that the endoscope and the device function as a single integrated apparatus. The device of the invention may cover most or all of the endoscope (including the distal end of the endoscope) to provide complete physical barrier between the endoscope and body tissues, thereby preventing the need for sterilization of the endoscope prior to the actual endoscopic procedure. The device of the invention may have additional slits or tubular channels (other than those for the passage of the film covering the lens to achieve a clear, unobstructed view during the endoscope use) to allow passage of endoscopic instruments such as biopsy forceps or brushes, air, fluids, or debris such as mucus or other bodily materials. Air may be removed from or pumped into the body cavity via such slits or channels that travel along the body of the device. Fluids may be removed from or irrigated into the body cavity via such slits or channels that travel along the body of the device. Debris may be removed from the body cavity via such slits or channels. Such slits or channels may have openings at the distal end of the device body, thereby allowing endoscopic instrumentation and allowing suction, irrigation, and other functions related to passage of air, fluids, and debris at the distal end of the endoscope.

Certain embodiments include additional openings, valves, dials, buttons, or controls of various designs near the proximal end of the device body (surrounding the proximal end of the endoscope), in the vicinity of the spools controlling the passage of the lens film, to allow passage of endoscopic instruments and/or to control the passage of air, fluids, or debris through the additional slits or channels that travel along and are an integral part of the device body.

Certain embodiments include a rigid device body while other embodiments include a flexible device body. Flexible device body design may be more appropriately used for flexible endoscopes.

A specific example of the current invention is: a device for maintaining a clear optical path immediately in front of the lens of an elongated viewing apparatus, the device comprising: an elongated hollow body defining comprising a proximal end and a distal end, wherein the elongated hollow body defines a lumen, wherein the elongated hollow body is adapted to receive the elongated viewing apparatus, a guide element disposed within the elongated hollow body, and a transparent lens cover film movably (for example slidably) associated with the guide element wherein the transparent lens cover film is threaded through and guided by the guide element so as to describe a preset travel path passing immediately in front of the lens of the elongated viewing apparatus.

Note that although the type of viewing apparatus described in the examples is generally elongated, thus requiring the device of the invention to be elongated, the current invention is not limited to en elongated embodiment. Additionally, the word "elongated" is not meant to limit the device to any particular dimensions, merely to indicate that the device has a length that generally exceeds its diameter, and the device of the invention encompasses all embodiments employing a means of removing debris from in front of a viewing device or an illuminating device.

Another specific example of the current invention is: a device for maintaining a clear optical path immediately in front of the lens of an elongated viewing apparatus, the device comprising: an elongated hollow body comprising a proximal end and a distal end, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus, and a frame/scaffold/lens cover film support means or specific distal device tip design to allow the surface of lens cover film become parallel to the surface of the lens of the elongated viewing apparatus.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the distal end is transparent and has a wall or bather separating the lumen from device exterior surface, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the distal end is transparent and has a wall or barrier separating the lumen from device exterior surface, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus.

Another specific example of the current invention is: a device for maintaining a clear optical path immediately in front of the lens of an elongated viewing apparatus, the device comprising: an elongated hollow body comprising a proximal end and a distal end, wherein the elongated hollow body defines a lumen, wherein the distal end is transparent and has a wall or barrier separating the lumen from device exterior surface, wherein the elongated hollow body is adapted to receive the elongated viewing apparatus, a guide element disposed within the elongated hollow body, a transparent lens cover film movably (for example slidably) associated with the guide element wherein the transparent lens cover film is threaded through and guided by the guide element so as to describe a preset travel path passing immediately in front of the transparent distal end of the device body and the lens of the elongated viewing apparatus, an additional guide element or additional guide elements disposed within the elongated hollow body for passage of air, fluids, debris, or endoscopic instruments.

Another specific example of the current invention is: a device for maintaining a clear optical path comprising an elongated hollow body with a proximal end and a distal end, wherein the elongated hollow body defines a lumen adapted to receive the viewing apparatus, a transparent lens cover film movably associated with the elongated hollow body so as to describe a preset travel path passing in front of the lens of the viewing apparatus and an endcap configured to engage opposing edges of the lens cover film in a sealing manner.

The term "immediately" does not limit the distance between the lens and the lens cover film, but merely implies that the lens cover film is positioned in front of the lens. It is expressly stated that other elements, such as a lens cover, may be present between the lens and the lens cover film. However, in certain embodiments, the lens cover may be absent.

Exemplary embodiments of the invention are described in detail by the figures and by the description below.

THE FIGURES

Further features and advantages will become apparent from the following and more particular description of the preferred embodiments of the disclosure, as illustrated in the accompanying drawings, and in which like referenced characters generally refer to the same parts or elements throughout the views, and in which:

FIG. 1 is a schematic longitudinal cross-section of the device showing the endoscope body (1), the objective lens (2), the lens cover film (3), the first spool (4) and the second spool (5).

FIG. 2A is a schematic view of one embodiment of the device showing the device body (6) wherein the device body defines internal guide channels (9) through which the lens cover film (3) is threaded. The lens cover film emerges out through a first guide slit (7), passes in front of the lens cover (22) and passes back into a second guide slit (8). In this view the endoscope body (1) and the objective lens (2) can be seen accommodated within the lumen of the device. The transparent lens cover (22) may be absent in other embodiments.

Figure 3:
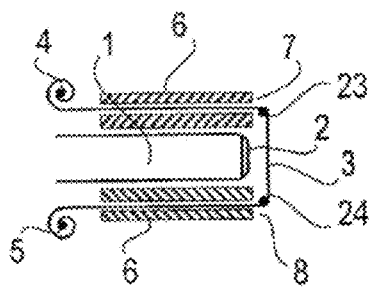

FIG. 3 is a schematic longitudinal cross-section of one embodiment of the device showing the endoscope body (1), the objective lens (2), the lens cover film (3), the first spool (4), the second spool (5), device body (6), first guide slit (7), second guide slit (8), upper frame supporting lens cover film (23), and lower frame supporting lens cover film (24). The lens cover film emerges out through a first guide slit (7), wraps around upper frame (23), passes in front of the lens (2), wraps around lower frame (24), and passes back into a second guide slit (8). In this view the endoscope body (1) and the objective lens (2) can be seen accommodated within the lumen of the device. The upper frame (23) and lower frame (24) allow the surface of the lens cover film (3) become parallel to the surface of objective lens (2). The lens cover (22) is not present in this embodiment and may be absent in other embodiments.

Figure 4A:
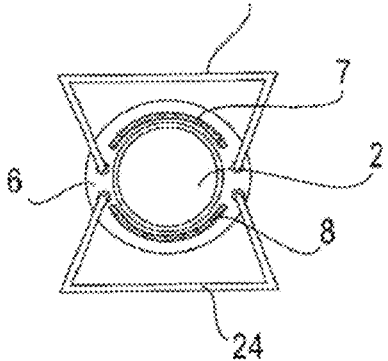

FIG. 4A is a schematic head-on view of the device showing the objective lens (2) inside the device body lumen, device body (6), a first guide slit (7), a second guide slit (8), upper frame supporting lens cover film (23), and lower frame supporting lens cover film (24). The lens cover film (3) is omitted in this figure in order to clearly demonstrate the 2 guide slits (with curvilinear or arc cross-sectional orientation in this embodiment). However, lens cover film (3) is present in and is an integral part of the present embodiment.

Figure 4B:
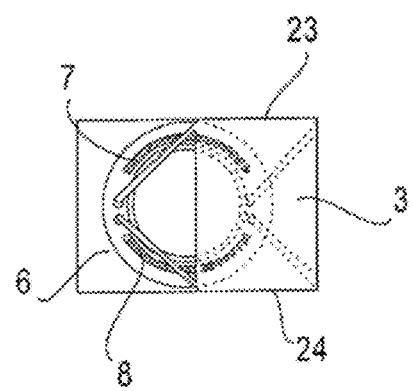

FIG. 4B is a perspective external view of the device showing the lens cover film (3) threaded out of the first guide slit (7), wraps around upper frame (23), passes in front of the objective lens (not shown), wraps around lower frame (24), and back into the second guide slit (8). The upper frame (23) and lower frame (24) are attached to device body (6) and allow the surface of the lens cover film (3) become parallel to the surface of objective lens (not shown).

Figure 5:
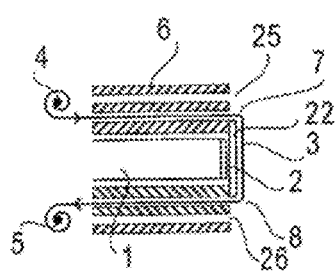

FIG. 5 is a schematic longitudinal cross-section of one embodiment of the device showing the endoscope body (1), the objective lens (2), the lens cover film (3), the first spool (4), the second spool (5), device body (6), first guide slit (7), second guide slit (8), transparent lens cover (22), first additional guide slit/channel (25), and second additional guide slit/channel (26). The 2 additional slits/channels traverse along the device body and may allow passage of air, fluids, debris, or endoscopic instruments. The lens cover film emerges out through a first guide slit (7), passes in front of the lens (2) and passes back into a second guide slit (8). In this view the endoscope body (1) and the objective lens (2) can be seen accommodated within the lumen of the device with transparent lens cover (22). The lens cover (22) may be absent in other embodiments.

Figure 6A:
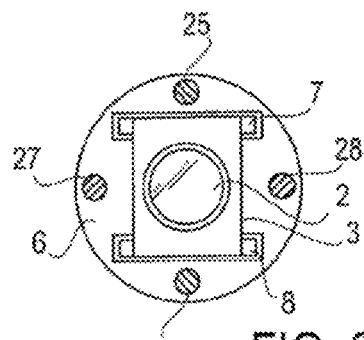

FIG. 6A is a schematic head-on view of the device showing the objective lens (2) inside the device body lumen, lens cover film (3), device body (6), a first guide slit (7), a second guide slit (8), first additional guide slit/channel (25), second additional guide slit/channel (26), third additional guide slit/channel (27), and fourth additional guide slit/channel (28). Any of the additional slits/channels may allow passage of air, fluids, debris, or endoscopic instruments. The number and location of the additional slits/channels may vary or may be absent in other embodiments. The transparent lens cover (22) is not shown but is present in certain embodiments including the present embodiment.

Figure 6B:
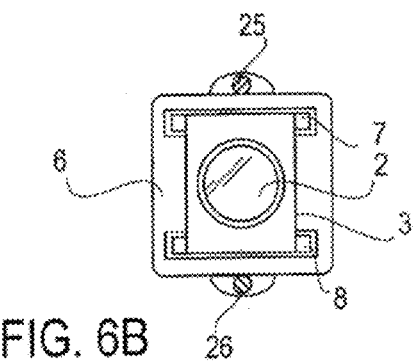

FIG. 6B is a schematic head-on view of the device showing the objective lens (2) inside the device body lumen, lens cover film (3), device body (6), a first guide slit (7), a second guide slit (8), first additional slit/channel (25), and second additional slit/channel (26). Any of the additional slits/channels may allow passage of air, fluids, debris, or endoscopic instruments. The number and location of the additional slits/channels may vary or may be absent in other embodiments. The transparent lens cover (22) is not shown but is present in certain embodiments including the present embodiment.

Figure 6C:
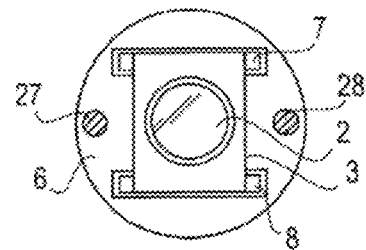

FIG. 6C is a schematic head-on view of the device showing the objective lens (2) inside the device body lumen, lens cover film (3), device body (6), a first guide slit (7), a second guide slit (8), first additional slit/channel (27), and second additional slit/channel (28). Any of the additional slits/channels may allow passage of air, fluids, debris, or endoscopic instruments. The number and location of the additional slits/channels may vary or may be absent in other embodiments. The transparent lens cover (22) is not shown but is present in certain embodiments including the present embodiment.

Figure 7A:
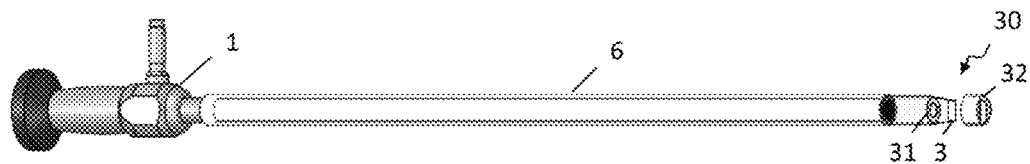

FIG. 7A is a perspective external view of one embodiment of the device showing the endoscope (1), device body (6) disposed over the elongated distal section of the endoscope, lens cover film (3) and an exploded view of alternative lens cover in the form of endcap (30) including proximal portion (31) and distal portion (32), such that film (3) is threaded between the proximal (31) and distal (32) portions in a sandwich configuration.

Figure 7B:
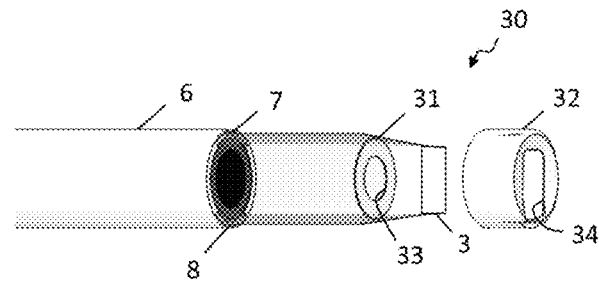

FIG. 7B is a perspective view showing details of endcap (30), with film (3) routed between the proximal (31) and distal (32) portions. When assembled, the proximal and distal surfaces of lens cover film (3) may be engaged by proximal (31) and distal (32) portions to seal against intrusion of fluids, while openings (33) and (34) provide a clear optical path for the objective lens (not shown in this view). Lens cover film (3) is routed through first guide slit (7) and second guide slit (8). Distal portion (32) may be sized to fit closely over the distal end of body (6) and attached or secured in any suitable manner.

Figure 8A:
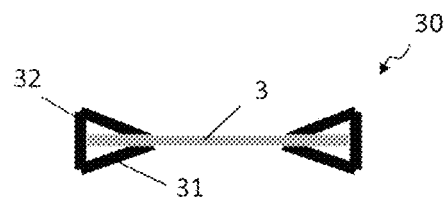

FIG. 8A is a schematic cross-section view of one embodiment showing the relationship between endcap (30) and lens cover film (3). Proximal portion (31) and distal portion (32) may be configured to engage lens cover film (3) between cooperating edges to stabilize it in a perpendicular orientation to the objective lens (not shown) as well as sealing it.

Figure 8B:
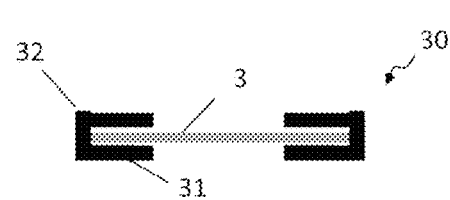

FIG. 8B is a schematic cross-section view of another embodiment showing proximal portion (31) and distal portion (32) of endcap (30) engaging lens cover film (3) between coplanar surfaces.

Figure 8C:
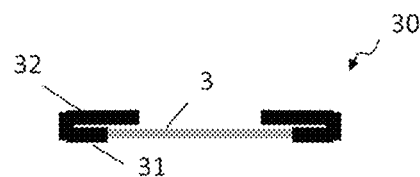

FIG. 8C is a schematic cross-section view of another embodiment showing distal portion (32) of endcap (30) engaging the exterior surface of lens cover film (3) and proximal portion (31) engaging the edges of lens cover film (3). In this embodiment, endcap (30) does not sandwich opposing surfaces of lens cover film (3).

Figure 8D:
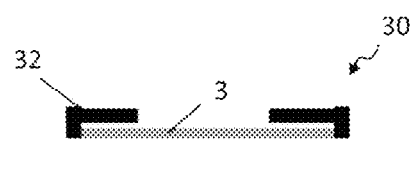

FIG. 8D is a schematic cross-section view of another embodiment showing distal portion (32) of endcap (30) engaging the exterior surface of lens cover film (3) and also engaging the edges of lens cover film (3). In this embodiment, endcap (30) does not sandwich opposing surfaces of lens cover film (3) and does not employ a proximal portion (31).

Figure 9A:
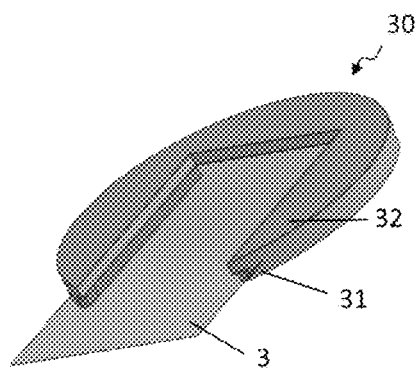

FIG. 9A is a perspective external view of one embodiment of the device showing endcap (30) and lens cover film (3). Proximal portion (31) and distal portion (32) may be integrated into one monolithic structure, or may be secured together during assembly. Edges of lens cover film (3) are sandwiched between proximal portion (31) and distal portion (32).

Figure 9B:
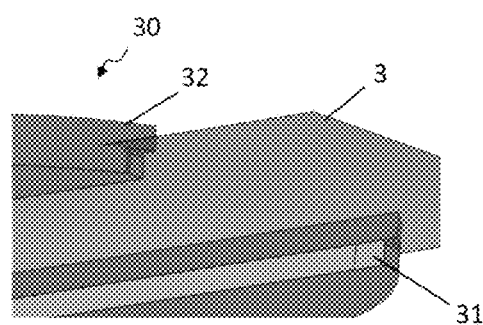

FIG. 9B is another perspective view of the embodiment of FIG. 9A showing the proximal surface of lens cover film (3) routed between proximal portion (31) and distal portion (32).

Figure 9C:

FIG. 9C is another perspective view of the embodiment of FIG. 9A, with the lens cover film removed. As shown, proximal portion (31) may be provided substantially only adjacent the edges of lens cover film to provide greater space for lens cover film to transition from the longitudinal orientation corresponding to its travel path along the device body to the perpendicular orientation in front of the objective lens.

Figure 10A:
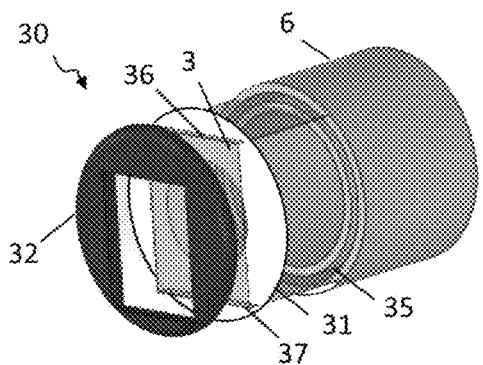

FIG. 10A is an exploded perspective external view of one embodiment of the device showing the distal end of device body (6) and lens cover film (3), with both feed and takeup paths routed through a single concentric lumen (35). Lens cover film (3) passes through parallel guides (36) and (37) in proximal portion (31). Distal portion (32) sandwiches lens cover film (3) against proximal portion (31) and rectangular opening (34) provides the optical path for the objective lens (not shown).

Figure 10B:
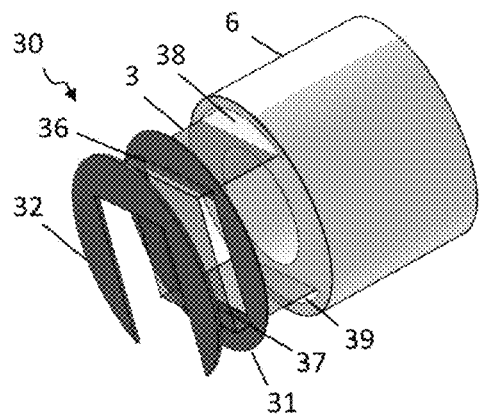

FIG. 10B is an exploded perspective external view of one embodiment of the device showing the distal end of device body (6) and lens cover film (3) routed through lumens (38) and (39) that have semi-circular configurations to provide a straight edge along the inner radius of the travel path of lens cover film (3). Lens cover film (3) passes through parallel guides (36) and (37) in proximal portion (31). Distal portion (32) sandwiches lens cover film (3) against proximal portion (31) and rectangular opening (34) features a cut-out along one edge to provide a fluid path to facilitate draining fluid and/or debris that may be deposited on the lens cover film (3).

Figure 11A:
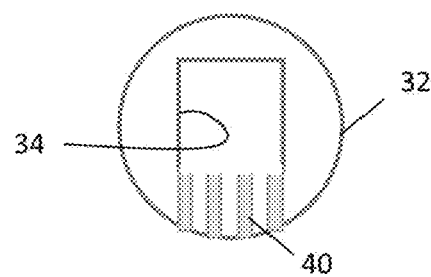

FIG. 11A is a schematic end view of another embodiment showing distal portion (32) of endcap (30) that features rectangular opening (34) and one or more channels (40) to facilitate draining fluid and/or debris that may be deposited on the lens cover film (not shown in this view).

Figure 11B:
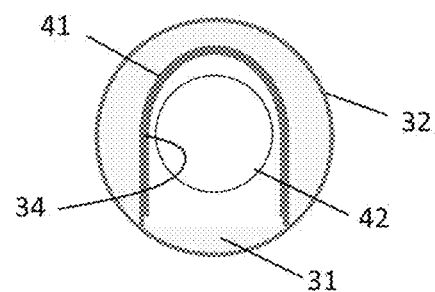

FIG. 11B is a schematic end view of another embodiment showing distal portion (32) of endcap (30) that features a horseshoe-shaped opening (34) to facilitate draining fluid and/or debris that may be deposited on the lens cover film (not shown in this view). Opening (34) may include a distally-projecting raised edge (41) to help protect the viewing filed by reducing or preventing the migration of fluid and/or debris over opening (34). In this embodiment, proximal portion (31) features window (42) rather than an opening. Window (42) may be formed from any material offering sufficient transparency to provide the desired optical path for the objective lens (not shown).

Figure 12A:
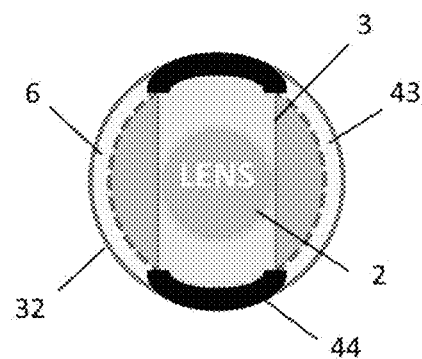

FIG. 12A is a schematic end view of another embodiment showing distal portion (32) of endcap (30). In this aspect, endoscope body (6) may include a light source (43). Distal portion (32) may include opaque and/or light absorbing sections (44) to reduce undesired transmission of light by lens cover film (3) that might otherwise distort the image.

Figure 12B:
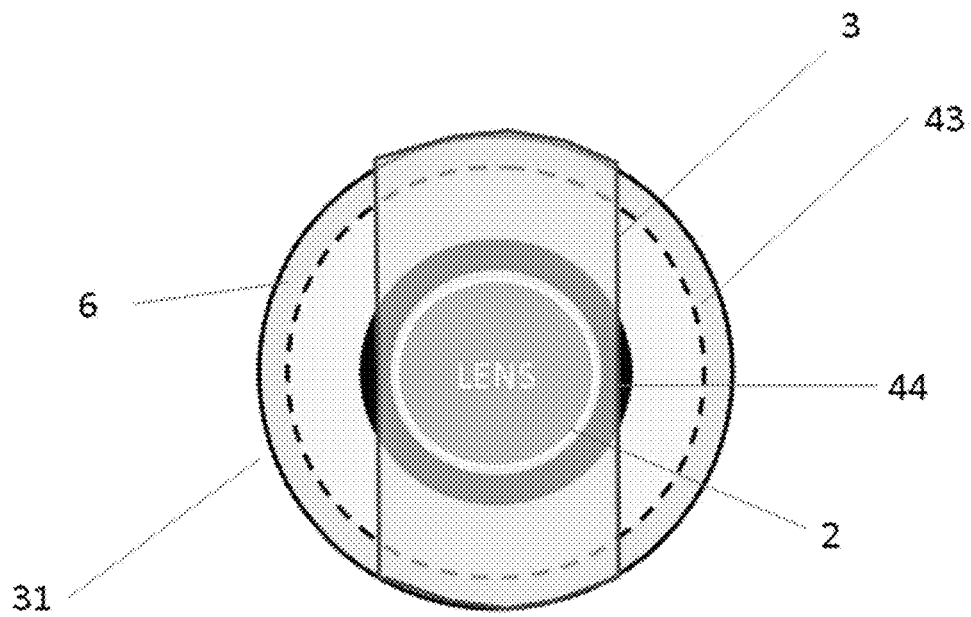

FIG. 12B is a schematic end view of another embodiment showing proximal portion (31) of endcap (30). In this aspect, endoscope body (6) may include a light source (43). Light reflection or scattering through film (3) may cause whiteness/haze and affect viewing quality. Edges around the opening of proximal portion (31) may include opaque and/or light absorbing sections/loop (44) to avoid high intensity light reflection or scattering.

Figure 12C:
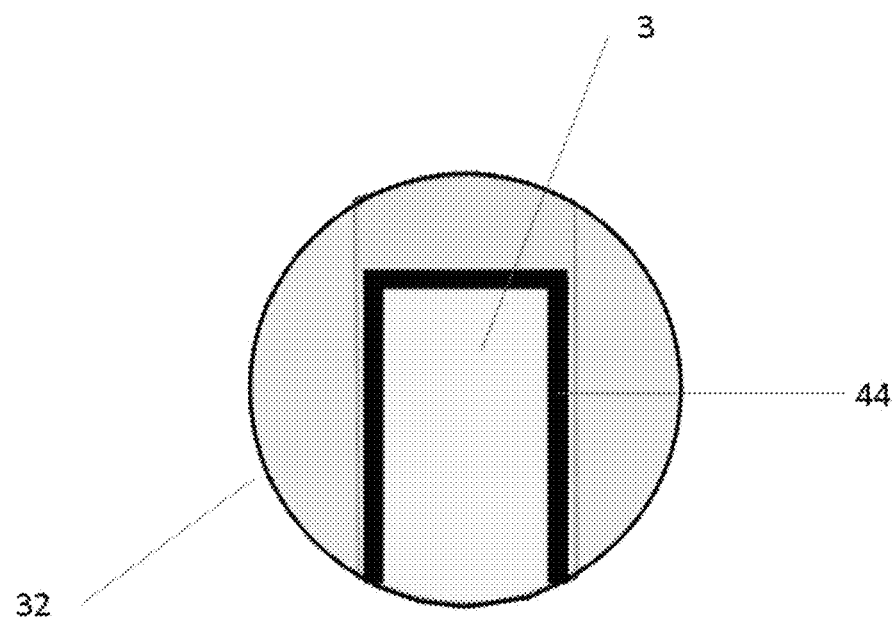

FIG. 12C shows distal portion (32) having opaque and/or light absorbing sections/loop (44) in edges around the opening to reduce undesired transmission of light by lens cover film (3).

Figure 13A:
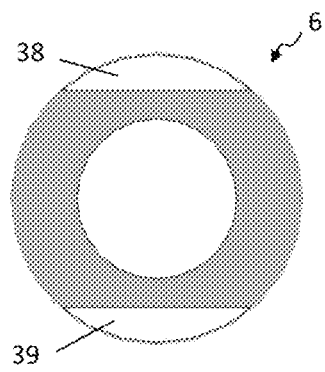

FIG. 13A is a schematic end view of another embodiment showing the distal end of device body (6) featuring semi-circular lumens (38) and (39) to provide straight edges along the inner radius of the travel path of lens cover film (not shown).

Figure 13B:
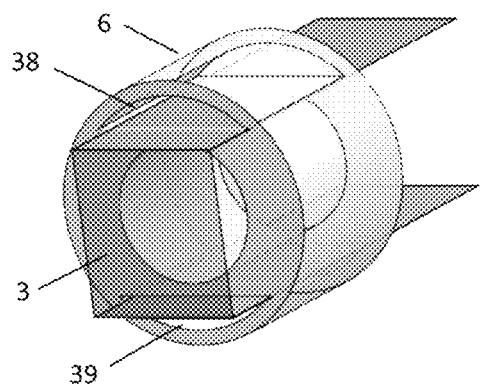

FIG. 13B is a perspective end view of the embodiment of FIG. 13A to illustrate the travel path of lens cover film (3).

The straight edges of lumens (38) and (39) guide lens cover film (3) to help avoid or minimize the formation of wrinkles.

Figure 13C:
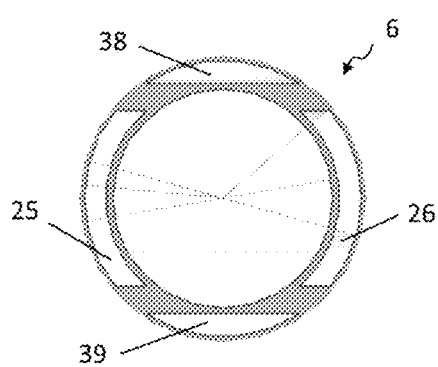

FIG. 13C is a schematic end view of an alternative embodiment of device body (6) that includes first additional slit/channel (25) and second additional slit/channel (26) to supplement semi-circular lumens (38) and (39). Any of the additional slits/channels may allow passage of air, fluids, debris, or endoscopic instruments.

Figure 13D:
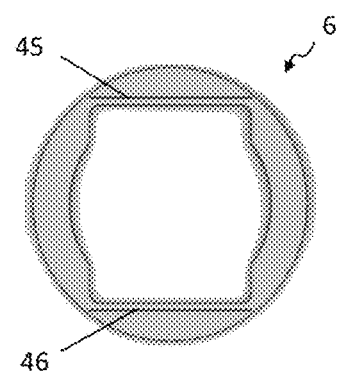

FIG. 13D is a schematic end view of an alternative embodiment of device body (6) that features parallel slits (45) and (46) rather than semi-circular lumens. Similarly, the straight edges of slits (45) and (46) guide lens cover film on its travel path.

Figure 13E:
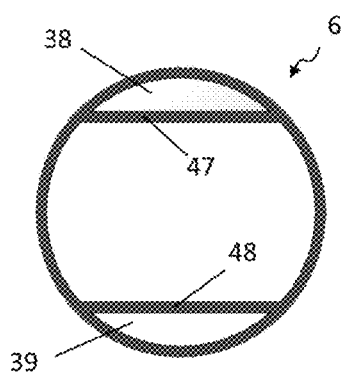

FIG. 13E is a schematic end view of an alternative embodiment of device body (6) in which semi-circular lumens (38) and (39) are formed by parallel walls (47) and (48). Again, the straight edges of lumens (38) and (39) guide lens cover film on its travel path.

Figure 13F:
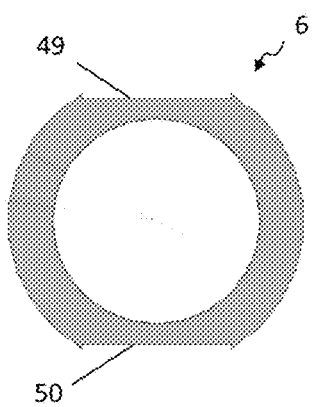

FIG. 13F is a schematic end view of an alternative embodiment of device body (6) in which at least the distal end of device body (6) has flattened sections (49) and (50). In this embodiment, lens cover film (not shown) is routed externally of device body (6) and the flattened sections (49) and (50) provide straight edges along the inner radius of its travel path.

Figure 14A:
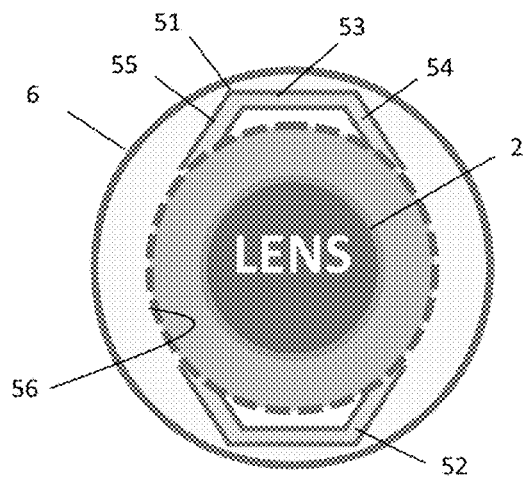

FIG. 14A is a schematic end view of another embodiment showing the distal end of device body (6) featuring shaped lumens (51) and (52). In one aspect, this configuration may be used to accommodate relatively wider lens cover film. For example, lumens (51) and (52) may have a central flat section (53) flanked by sections (54) and (55) that angle towards the lumen (56) of device body (6) in which objective lens (2) is disposed. As can be seen, flat section (53) and angled sections (54) and (55) conform to the circular profile of device body (6).

Figure 14B:
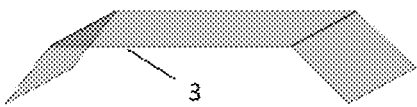

FIG. 14B is a schematic perspective view of lens cover film (3) for use with the embodiment shown in FIG. 14A. Lens cover film (3) may have a pre-shaped configuration to match shaped lumens (51) and (52) or otherwise may be sufficiently flexible to conform to the lumens.

Figure 15A:
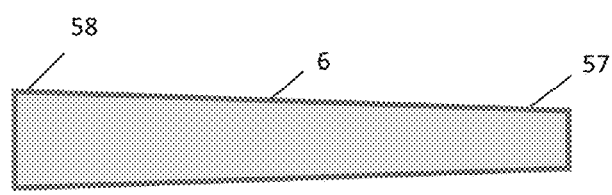

FIG. 15A is a schematic longitudinal cross-section of one embodiment of device body (6) showing a gradual taper from a proximal end (57) having a relatively smaller diameter to a distal end (58) having a relatively greater diameter. The increased diameter of device body (6) at the distal end may facilitate routing lens cover film while minimizing wrinkling.

Figure 15B:
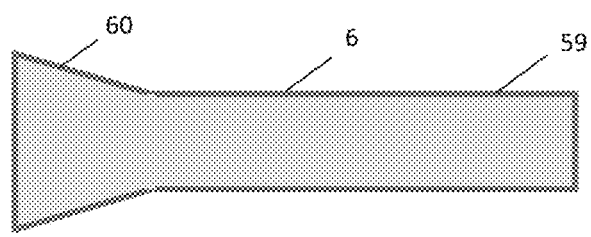

FIG. 15B is a schematic longitudinal cross-section of another embodiment of device body (6) showing a relatively constant diameter proximal section (59) and a flared distal end (60), also to provide an increased diameter to minimize wrinkling of lens cover film along its travel path.

Figure 16A:
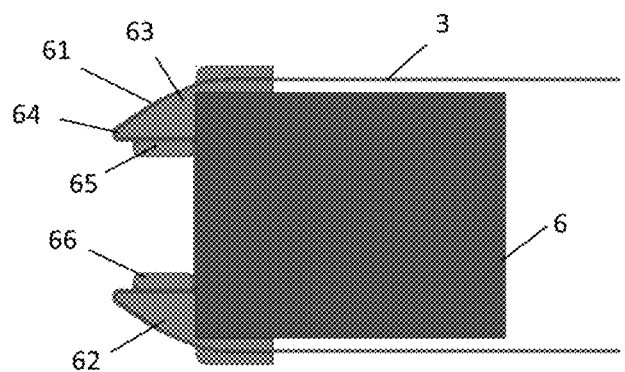

FIG. 16A is a schematic longitudinal cross-section showing the distal end of one embodiment of device body (6). Lens cover film (3) may have an arc-shaped configuration in portions of its travel path longitudinally along device body (6). The distal end of device body (6) may feature projections (61) and (62) to help guide lens cover film (3) from this arc-shaped configuration to a flat configuration when in front of the objective lens. Projections (61) and (62) may include a proximal section (63) having an arc-shaped profile matching the configuration of lens cover film (3) that transitions to a distal section (64) having a straight edge. Inner guide rails (65) and (66) may further help route lens cover film (3) over projections (61) and (62) and in front of the objective lens (not shown).

Figure 16B:
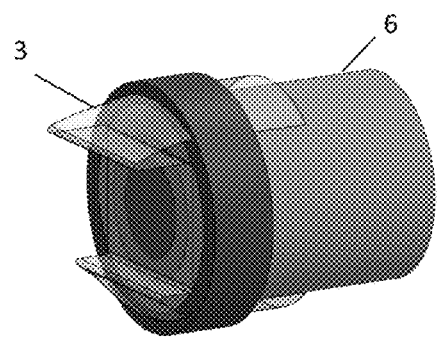

FIG. 16B is a schematic perspective view of the embodiment shown in FIG. 16A. Projections (61) and (62) have been removed to help illustrate the travel path of lens cover film (3). As shown, lens cover film (3) transitions from an arc-shaped configuration corresponding to the profile of device body (6) to a flat configuration at a location corresponding to the straight edges of the distal sections (64) of projections (61) and (62). Inner guide rails (65) and (66) to illustrate that lens cover film (3) is routed in a flat configuration across the lumen of device body (6).

Figure 16C:
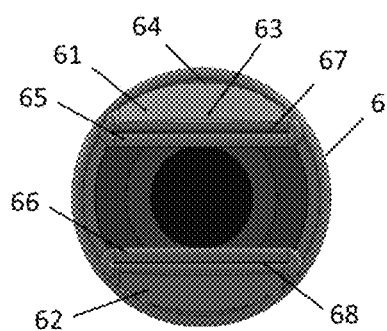

FIG. 16C is a schematic end view of the embodiment shown in FIG. 16A. As noted, projections (61) and (62) feature arc-shaped proximal section (63) that transitions to straight-edged distal section (64). Inner guide rails (65) and (66) define slits (67) and (68) through which the lens cover film may be routed through. Lens cover film also travels under inner guide rails (65) and (66) to stabilize it in front of the objective lens.

Figure 17A:
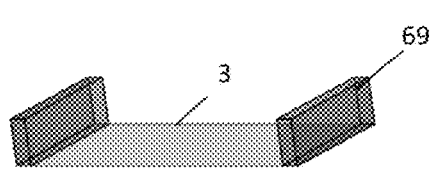

FIG. 17A is a schematic perspective view of an embodiment of lens cover film (3) having edges (69) with increased thickness to improve sealing with endcap (30).

Figure 17B:
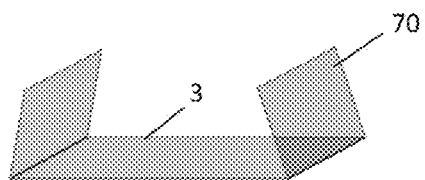

FIG. 17B is a schematic perspective view of an embodiment of lens cover film (3) having pre-shaped edges (70) to improve sealing with endcap (30).

Figure 17C:
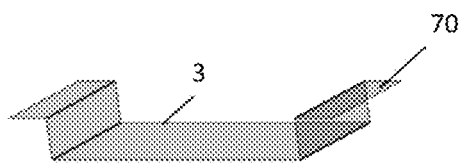

FIG. 17C is a schematic perspective view of another embodiment of lens cover film (3) having pre-shaped edges (70) to improve sealing with endcap (30).

Figure 17D:
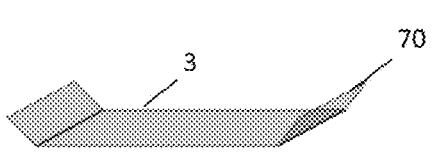

FIG. 17D is a schematic perspective view of another embodiment of lens cover film (3) having pre-shaped edges (70) to improve sealing with endcap (30).

Figure 18:
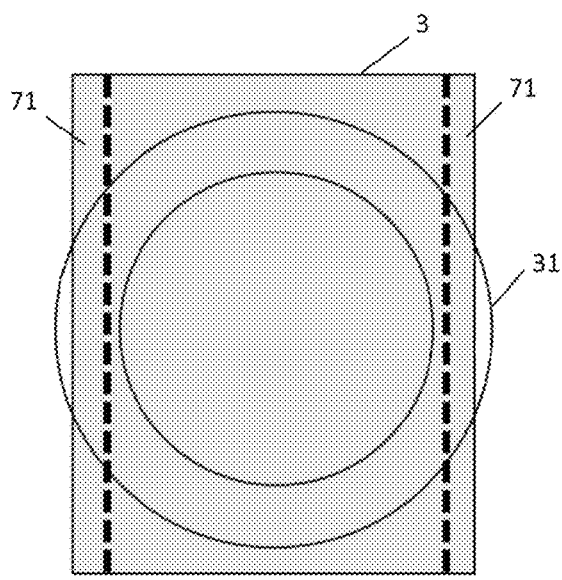

FIG. 18 is a schematic end view of an embodiment showing lens cover film (3) having adhesive regions (71) along its edges that engages with the surface of the proximal portion (31) to improve sealing with endcap (30). The adhesive regions (71) may have a slight adhesive property that may be activated, such as by pressure, once the lens cover film (3) is in position in front the lens (not shown).

Figure 19:
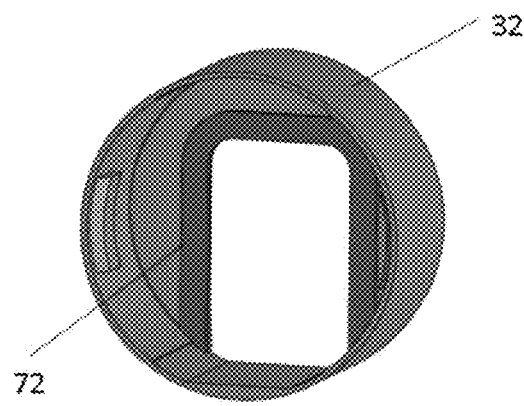

FIG. 19 is a perspective view showing sealing pad (72) with endcap (30). Sealing pad (72) can be squeezed as a thin barrier between proximal portion and distal portion to block infiltration.

FIGS. 20A-D illustrate the lens cover design in one preferred embodiment of the invention.

Figure 20A:
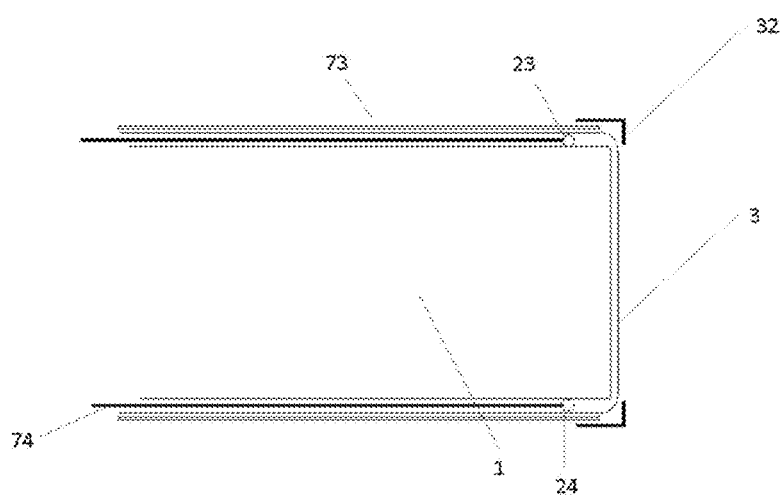

FIG. 20A is a cross-sectional side view of the distal portion of the current device attached to the distal end (distal lens) of the laparoscope, showing lens cover film of device (3), outer sheath of device body (73), inner sheath of device body (74), nitinol frame (23, 24), cap of device (32), and laparoscope (1). The device body with its inner sheath (74) has a lumen that accommodates the body and distal portion of the laparoscope (1). The film (3) is positioned between the inner sheath (74) and outer sheath (73) of the device body and travels in front of the laparoscope lens to cover the lens surface (thereby protecting the lens surface from soiling during laparoscope use), and the path of the film is preset so that it exits from the inner/outer sheaths of the dorsal/top portion of the device body (74/73), travels in front of the laparoscope lens, and enters inner/outer sheaths of the ventral/bottom portion of the device body (74/73) as the film is rolled in a uni-directional movement. A cap as distal portion (32) is present to provide additional coverage of the laparoscope lens—by preventing entry of debris/materials/fluids around/along the film edges to soil the laparoscope lens. A nitinol component (23, 24) may be present to allow flattening of the film as it transitions from the device body sheaths (74/73) to the area in front of the laparoscope lens, although such component may be absent in certain embodiments of the present device. In FIG. 20A, the nitinol component is at a distance proximal to/away from the laparoscope lens.

Figure 1:
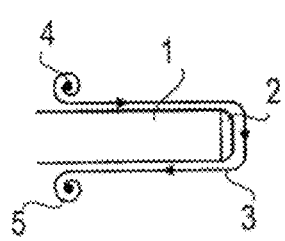
Figure 2A:
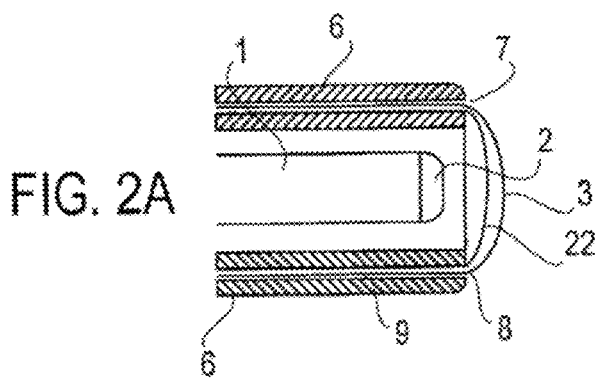
FIG. 2B is a schematic head-on view of the device showing the endoscope body (1), the objective lens (2), the lens cover film (3), device body (6), a first guide slit (7), a second guide slit (8). The lens cover (22) is not shown in this figure.
FIG. 2C is a perspective external view of the device showing the lens cover film (3) threaded out of the first guide slit (7) and back into the second guide slit (8), passing in front of the objective lens (not shown).
Figure 2B:
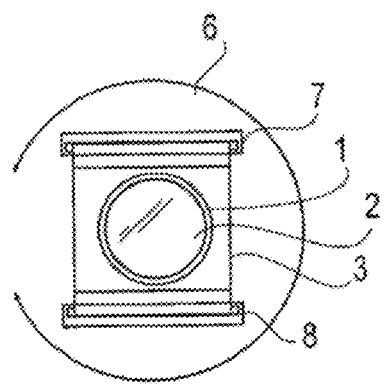
Figure 2C:
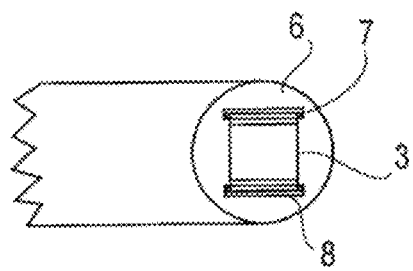
Figure 20B:
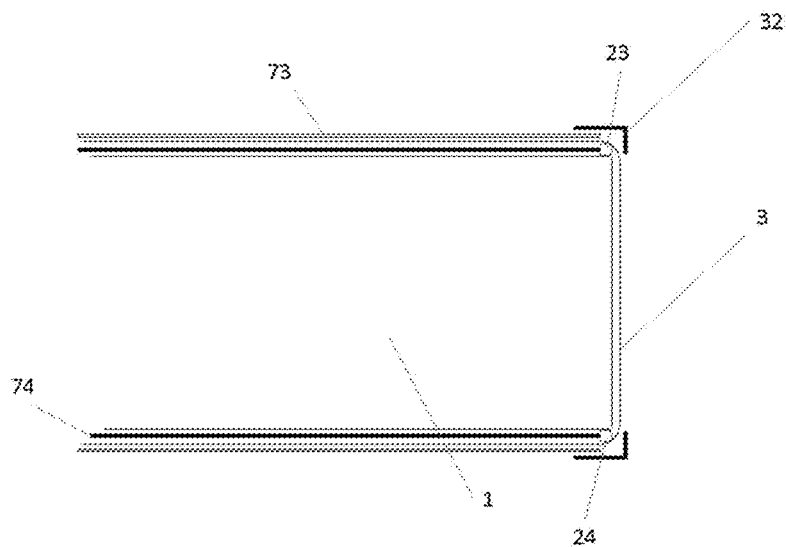

FIG. 20B is a cross-sectional side view of another variation of the distal portion of the current device attached to the distal end (distal lens) of the laparoscope, showing lens cover film of device (3), outer sheath of device body (73), inner sheath of device body (74), nitinol frame (23, 24), cap of device (32), and laparoscope (1). The design is similar to that illustrated in FIG. 20-1A. However, in the present variation of the device, the nitinol component (23, 24) is positioned near/at the laparoscope lens. It should be noted that in other embodiments of the present device, the nitinol component may be entirely absent or located at a different position in relation to the laparoscope lens—such as a position distal to the laparoscope lens (not shown).

Figure 20C:
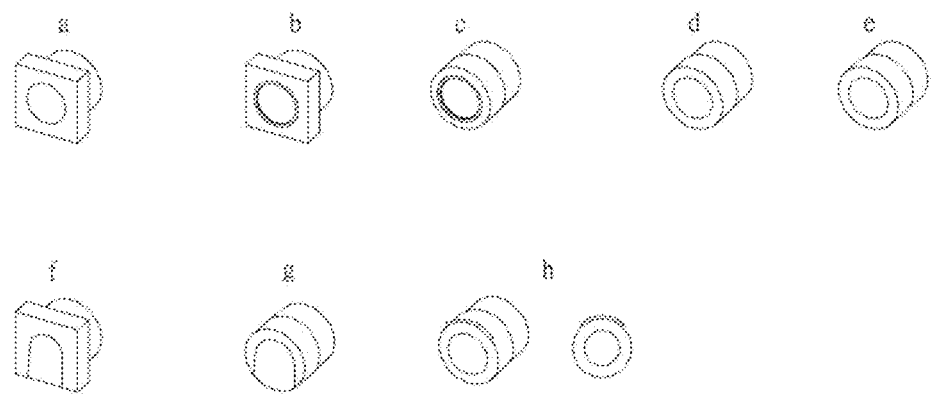

FIG. 20C illustrates 3-dimensional views of multiple exemplary variations of the cap component as distal portion (32) of the present device embodiment shown previously in FIGS. 20A and 20B. The cap (32) may be square or rectangular (as in insets (a), (b), and (f)) or round (as in insets (c), (d), (e), (g) and (h)). The cap component may have an opening/cut-away portion at its ventral/bottom aspect as in inset figures (f) and (g)—to facilitate movement of fluids/debris away from the laparoscope lens and device body sheaths (74/73) near the ventral/bottom aspect of the laparoscope-device assembly. The cap component may have a raised edge/rim at the dorsal/upper portion as in inset (h) as shown in the additional end view to prevent downward dripping movement of debris/fluids to soil the laparoscope lens/device cover film.

Figure 20D:
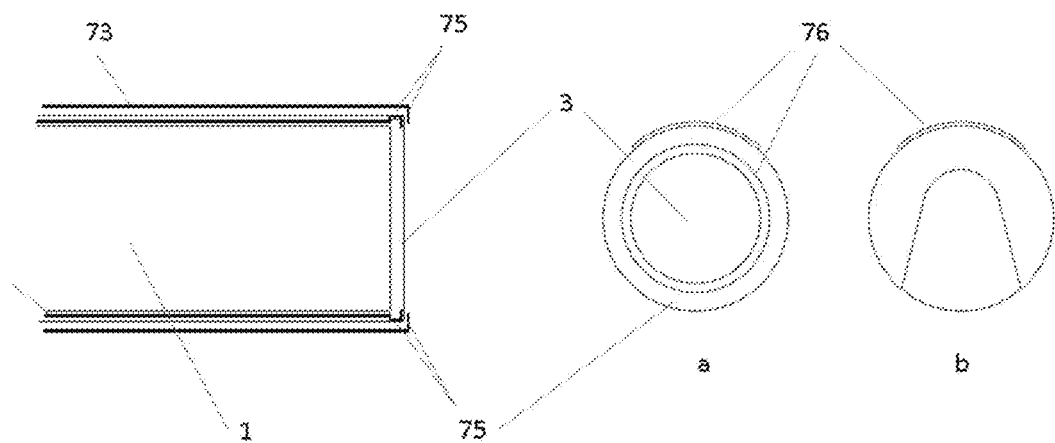

FIG. 20D is a cross-sectional side view of the distal portion of another embodiment of the current device attached to the distal end (distal lens) of the laparoscope, showing lens cover film of device (3), outer sheath of device body (73), inner sheath of device body (74), rim of device (75), and laparoscope (1). The device body with its inner sheath (74) has a lumen that accommodates the body and distal portion of the laparoscope (1). The film (3) is positioned between the inner sheath (74) and outer sheath (73) of the device body and travels in front of the laparoscope lens to cover the lens surface (thereby protecting the lens surface from soiling during laparoscope use), and the path of the film is preset so that it exits from the inner/outer sheaths of the dorsal/top portion of the device body (74/73), travels in front of the laparoscope lens, and enters inner/outer sheaths of the ventral/bottom portion of the device body (74/73) as the film is rolled in a uni-directional movement. A rim (75) is present to provide additional coverage of the laparoscope lens—by preventing entry of debris/materials/fluids around/along the film edges to soil the laparoscope lens. The rim component (75) may be part of the device outer sheath (73), or it may be a separate component attached to the outer sheath (73) of the device. In the present embodiment of the device, the rim has 2 layers—outer layer (R) and inner layer (Ri)—and the film (3) travels between these 2 layers of rim (R and Ri). The inner sheath (74) is recessed (ie—with a longitudinal length that is shorter than that of outer sheath and does not extend to the laparoscope lens vicinity) to facilitate transformation of the film (3) from a hemispheric configuration within outer-inner sheaths to a flat configuration in front of the laparoscope lens. Inset (a) is a 3-dimensional view of the embodiment illustrated in FIG. 20D, showing the lens cover film (3) and rim (75). A raised edge (76) may be present at the top/dorsal aspect of the rim to prevent downward dripping movement of debris/fluids as shown in the inset picture, although such feature may be absent in other embodiments of the invention. Inset (b) is a 3-dimensional view of the embodiment illustrated in FIG. 20D, showing the lens cover film (3) and a different variation of the rim (75)—in which the ventral/bottom aspect of the rim (75) has an opening/cut-away portion—to facilitate movement of fluids/debris away from the laparoscope lens and device body sheaths (74/73) near the ventral/bottom aspect of the laparoscope-device assembly.

FIGS. 21A-K illustrate the lens cover design in one preferred embodiment of the invention. In this embodiment, the 3 key components of the endcap (30) of the present invention—a proximal portion (31) (preferably transparent), a distal portion (32), and a sheath design—are illustrated.

Figure 21A:
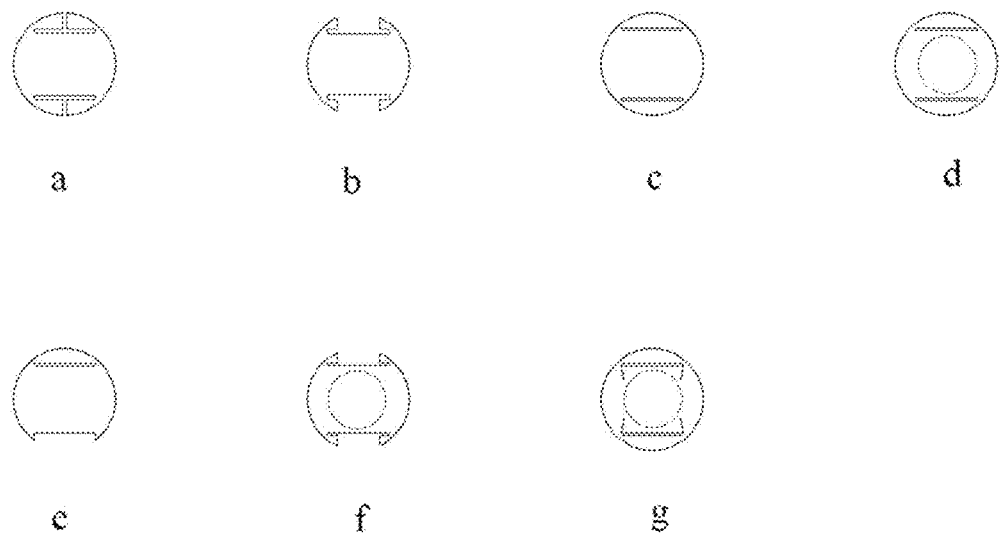

FIG. 21A illustrates front views of other variations of the transparent proximal portion (31) of the present device, with various slit-slit, groove-groove, and combined slit-groove designs. Inset (a) shows a transparent proximal portion with a partially open top slit and a partially open bottom slit. Inset (b) shows a transparent distal portion with a partially closed top groove and a partially closed bottom groove. Inset (c) shows a transparent proximal portion with a top slit and a bottom slit. Inset (d) shows a transparent proximal portion with a rim of a different material composition, and the rim has a top slit and a bottom slit. Inset (e) shows a transparent proximal portion with a top slit and a bottom groove. Inset (f) illustrates a transparent proximal portion with a rim of a different material composition, and the rim has a top partially open slit and a bottom partially open slit. Inset (g) shows a transparent proximal portion with a slanted/flat top edge and a slanted/flat bottom edge—in which the film of the device comes in contact with and moves along the slanted/flat edges of the transparent proximal portion. It should be noted that the slits/grooves described above are designed to facilitate flattening of the device film in front of the laparoscope lens.

Figure 21B:
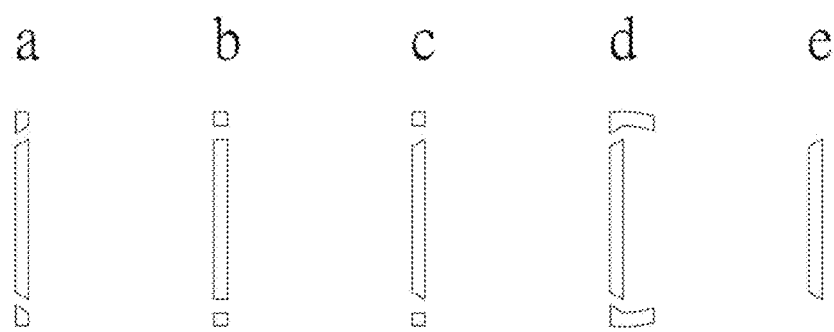

FIG. 21B illustrates the side views of other variations of slit/groove/opening design of the transparent proximal portion of the present device, which are shown in insets a, b, c, d, and e.

Figure 21C:
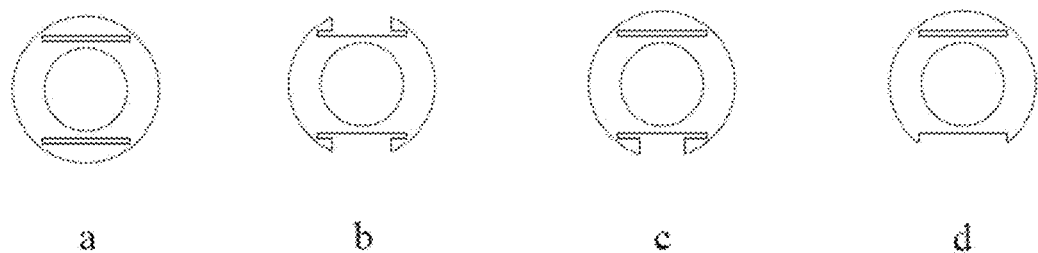

FIG. 21C illustrates a barrier ring design as an alternative to the transparent proximal portion—which prevents distal movement of the laparoscope lens towards the film. The ring has a hollow lumen that allows unobstructed viewing field in front of the laparoscope lens, and it is sandwiched between the laparoscope lens and the film of the device. The ring may be associated with various slit-slit, groove-groove, and slit-groove designs that allow passage of a flat film in front of the laparoscope lens, and the front views of 4 examples of the ring barrier are shown in insets (a), (b), (c) and (d).

Figure 21D:
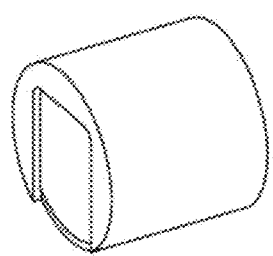

FIG. 21D is a 3-dimensional view of the distal portion (32) of the present device. The cut-away portion is located at the ventral/bottom aspect of the cap component, and such design facilitates movement of fluids/debris away from the laparoscope lens and device body near the ventral/bottom aspect of the laparoscope-device assembly.

Figure 21E:
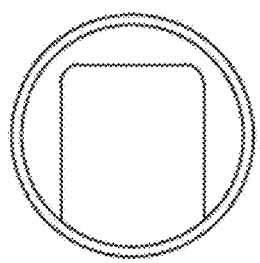

FIG. 21E is a front view of the distal portion (32) illustrated in FIG. 21D. The distal portion (32) is shown to cover the lateral and dorsal (top) aspects of the transparent proximal portion (31).

Figure 21F:
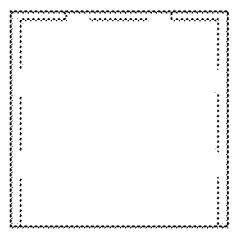

FIG. 21F is a top view of the cap component illustrated in FIG. 21D.

Figure 21G:
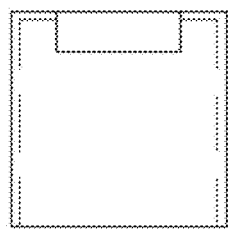
Figure 21G:
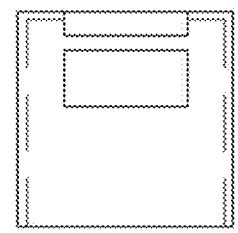

FIG. 21G illustrates the bottom view of the distal portion (32) illustrated in FIG. 21D. Inset (a) shows the cut-away portion of the ventral (bottom) aspect of the distal portion. Inset (b) shows a variation of the cut-away design at the ventral aspect of the distal portion.

Figure 21H:
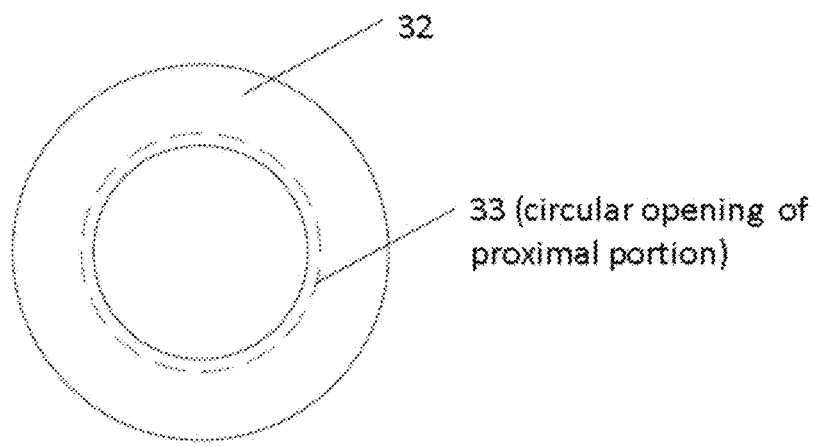

FIG. 21H illustrates an alternative distal portion design, in which there is no cut-away portion shown in FIG. 21D.

Figure 21I:
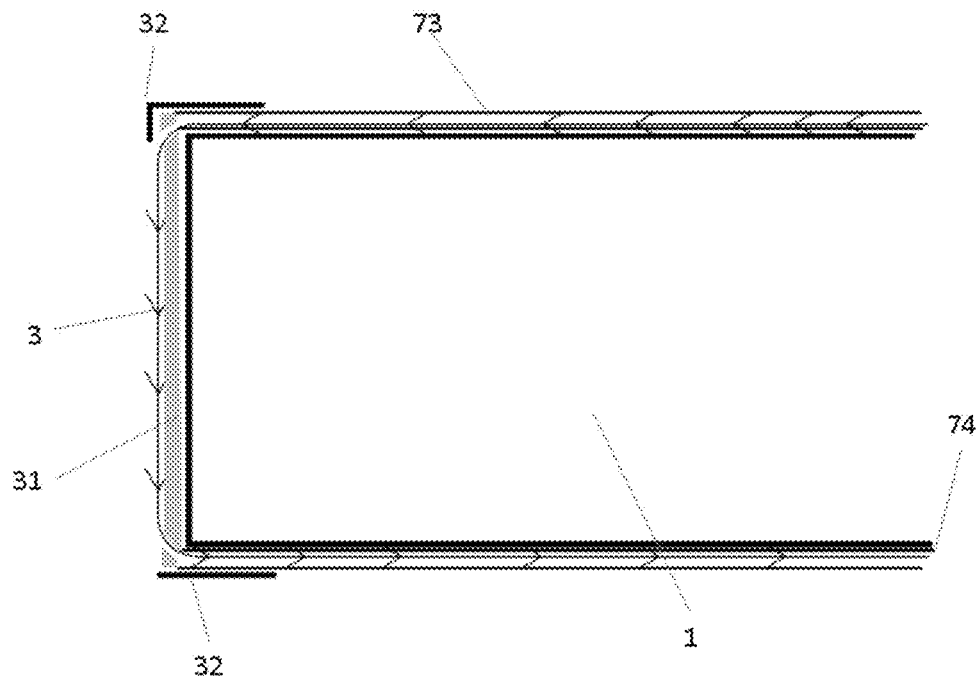

FIG. 21I illustrates another example of "transparent proximal portion"-"distal portion"-"sheath" combination in the present device design, in which a cross-sectional view of the device-laparoscope assembly is illustrated. A distal portion (32) (with a cut-away portion at its bottom/ventral aspect) is present to prevent movement of fluids/debris into the space behind the film (3). A transparent proximal portion (31) with dorsal/top and ventral/bottom slits/grooves is present between the film and the laparoscope lens. Arrows illustrate the direction of the film movement.

Figure 21J:
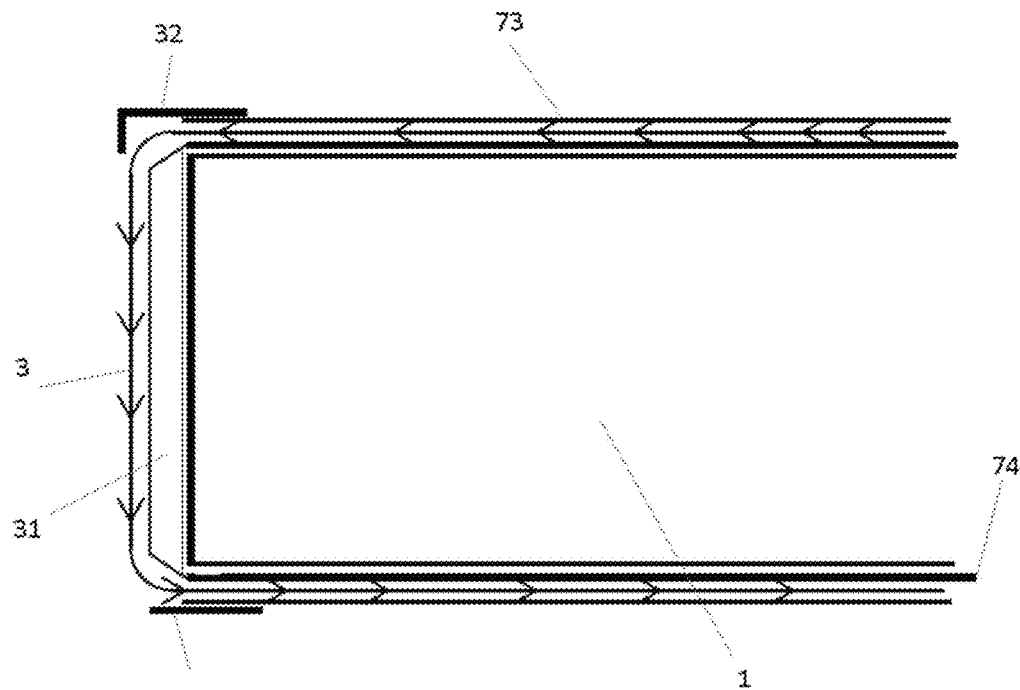

FIG. 21J illustrates another example of "transparent proximal portion"-"distal portion"-"sheath" combination in the present device design, in which a cross-sectional view of the device-laparoscope assembly is illustrated. A distal portion (32) (with a cut-away portion at its bottom/ventral aspect) is present to prevent movement of fluids/debris into the space behind the film (3). A transparent proximal portion (31) with dorsal/top and ventral/bottom slanted edges is present between the film and the laparoscope lens. Arrows illustrate the direction of the film movement.

Figure 21K:
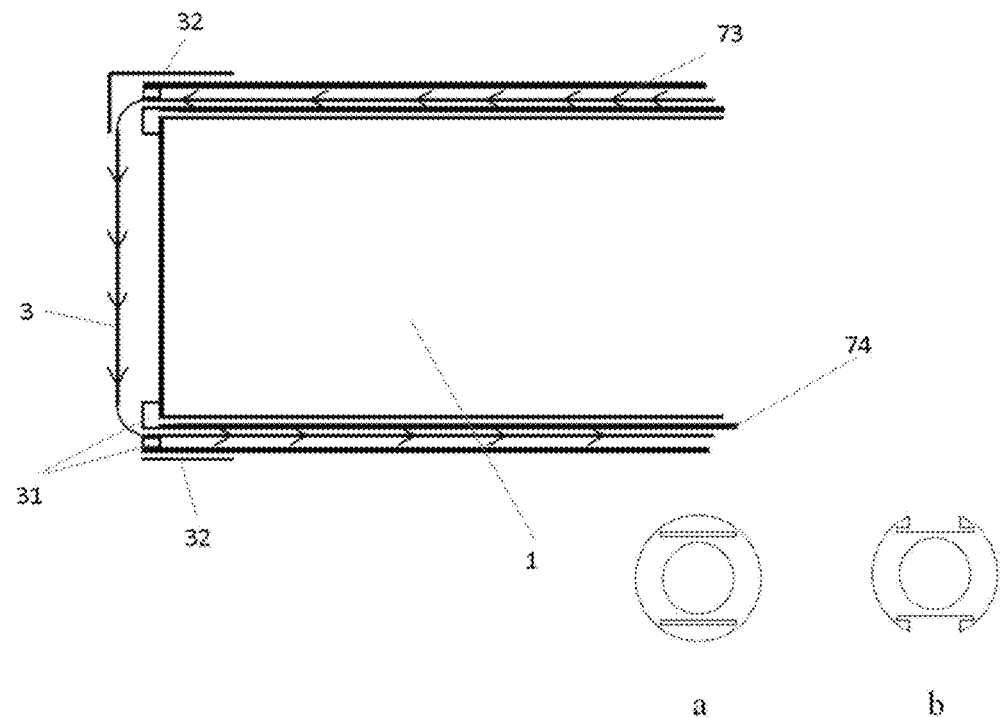

FIG. 21K illustrates another example of "proximal portion"-"distal portion"-"sheath" combination in the present device design, in which a cross-sectional view of the device-laparoscope assembly is illustrated. A distal portion (32) (with a cut-away portion at its bottom/ventral aspect) is present to prevent movement of fluids/debris into the space behind the film (3). A ring proximal portion (31) (shown as "catch ring" with hollow central lumen in front of the laparoscope lens) with dorsal/top and ventral/bottom slits/grooves is present as inset (a) and (b) between the film and the laparoscope lens. Arrows illustrate the direction of the film movement.

Figure 22:
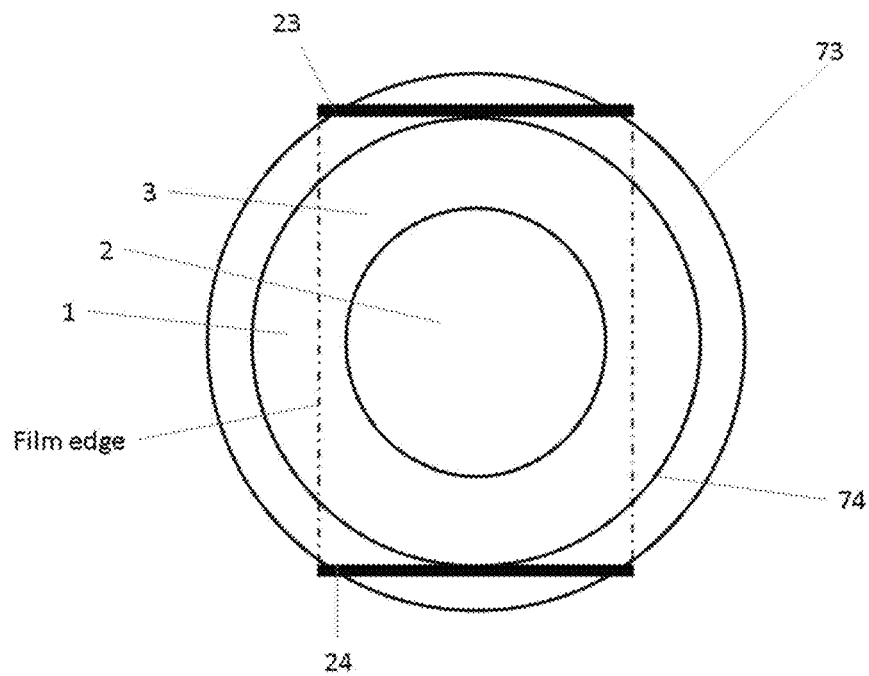

FIG. 22 is a front view of an embodiment of the present device mounted to a 10 mm laparoscope. Laparoscope viewing field is approximately 3 mm in radius. Given the above, a film with at least 0 to 2 mm beyond/lateral to the edge of the viewing field can be passed in front of the laparoscope lens (2) to provide adequate coverage of the lens. Flattening of the film in front of the laparoscope lens (2) is facilitated by the use of a scaffold/frame (23, 24) (which may be made of nitinol) positioned at dorsal/top aspect and ventral/bottom aspects of the device.

Figure 23A:
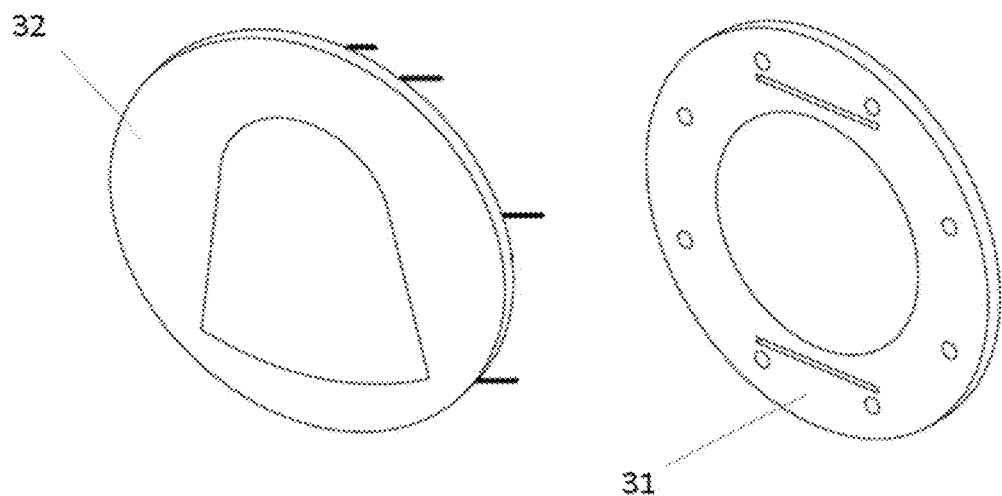
Figure 23B:
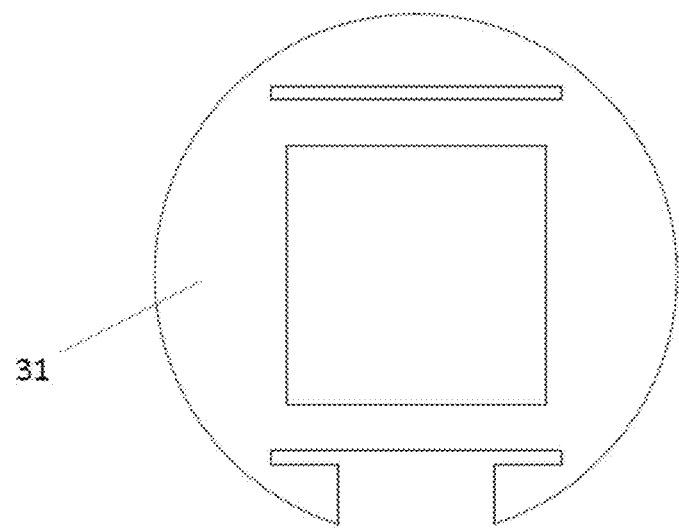

FIG. 23A illustrates one example of endcap (30) association. Such association may be in the form of physical attachment via a mechanical design that is based on protrusion-hole (male-female) interlocking components, as shown. FIG. 23B is a front view of another variation of the proximal portion (31) of the present device, with a top slit and a bottom groove. The central lumen may be circular or rectangular among various device embodiments.

Figure 24A:
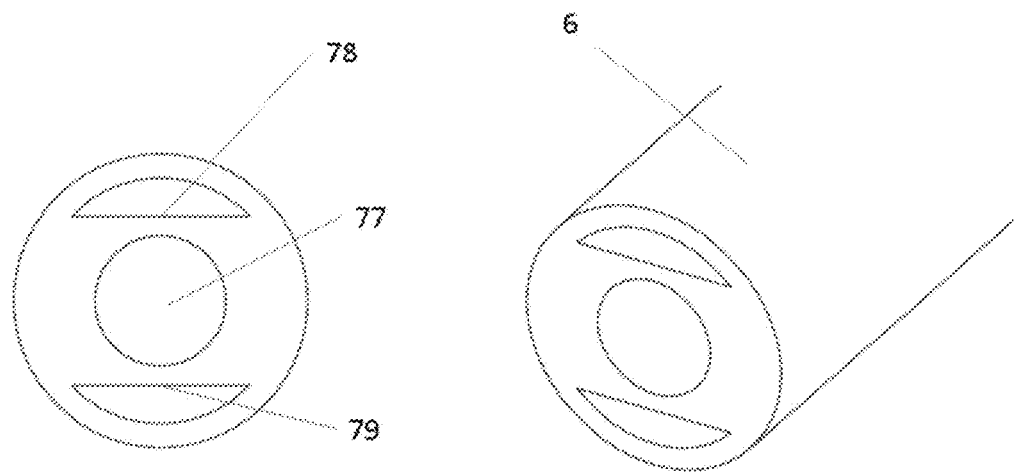

FIG. 24A shows a 3-dimensional view of the distal device body (6) and a corresponding front view of the distal device body in one embodiment of the device, with a central lumen (77) (accommodating laparoscope body), a top/dorsal guide element (78) and a bottom/ventral guide element (79) allowing film passage.

Figure 24B:
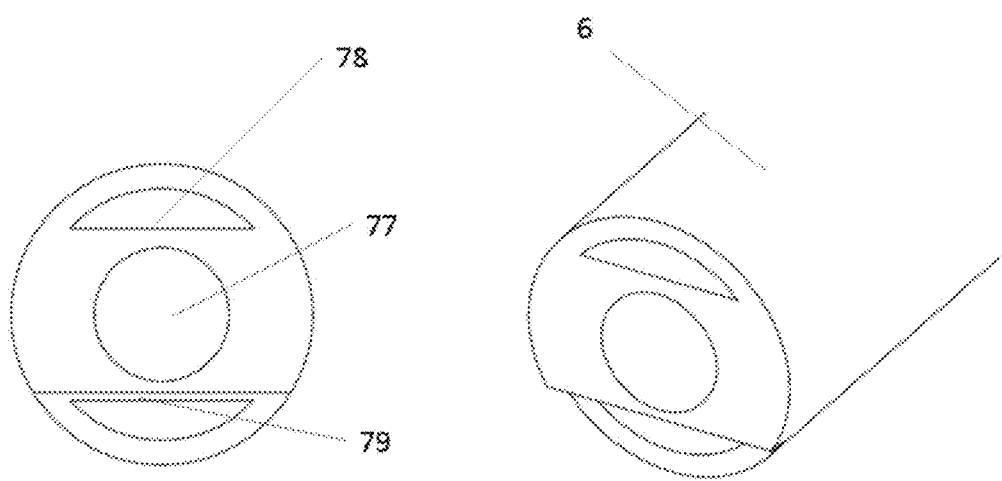

FIG. 24B is a 3-dimensional view of the distal device body (6) and a corresponding front view of the distal device body in another embodiment of the device, with a central lumen (77) (accommodating laparoscope body), a top/dorsal guide element (78) and a bottom/ventral guide element (79) allowing film passage. The bottom guide element (79) is recessed, and such design facilitates movement of debris/fluids away from the laparoscope lens/device body as the soiled film with debris/fluids is moved towards the ventral/bottom aspect of the cap.

DETAILED DESCRIPTION

Various embodiments are shown in FIGS. 1-24. In one embodiment the invention is a device comprising a hollow device body (6) that is designed to fit over an endoscope. The body of the device may be rigid or flexible. The body of the device may be sufficiently flexible so as to conform and mold to the contour of the endoscope. Such flexibility may be achieved by using a soft, elastic material such as latex, rubber, plastic, or a woven fabric comprising latex or other elastic fibers. The hollow device body defines a lumen shaped and sized to receive an endoscope of a particular desired size. The distal end of the device body may be open or may be closed by means of a transparent window or lens cover (22). The device body (6) may define one or more internal guide channels (9), through some of which the lens cover film (3) is threaded. The lens cover film emerges out through a first guide slit (7), passes in front of the lens cover (22) and objective lens (2), and passes back into a second guide slit (8). Guide slits 7 and 8 are preferably parallel. The entire apparatus may also be designed to fit within a trocar.

Certain embodiments include a lens cover film that is wound onto a spool. For example, a flexible lens cover film (3) may be rolled onto a first spool (4) and systematically unrolled such that it passes in front of the objective lens (2) of the endoscope (1). The lens cover film (3) can be unrolled as needed to provide a clean and clear lens cover in front of the objective lens (2). The leading end of the lens cover film may be captured and wound onto on a second spool. By winding the lens cover film onto the second spool (5) the lens cover film is pulled from the first spool, along a pre-set travel path, passing in front of the objective lens, and wound onto the second spool. The spools may be positioned at any convenient location within or external to the device. The means of winding, unwinding, or moving the lens cover film may comprise many different design variations including spools, winches, geared mechanisms, manually operated and electrically operated elements. Although spools are described in various exemplary embodiments, the invention does not require that spools be used and the lens cover film may be retained by, released from, and captured by any suitable means. Designs of such means will be readily apparent to those of skill. For example the lens cover film may be retained in a folded configuration, folded up upon itself prior to release into a pre-set travel path.

In one aspect, lens cover film (3) may have high optical clarity. As will be appreciated, luminous transmittance and haze may affect viewing clarity. In general, a film with luminous transmittance over 85% and haze less than 5% may be used. For example, a Mylar (boPET) film which has luminous transmittance over 88% and haze less than 4% may be employed. Film with higher optical quality may also be used to provide better viewing quality. For example, a boPET film with very low haze (e.g., 1%) may be used. The film (e.g., boPET) may also have relatively high water contact angle so it has hydrophobic characteristics.

The travel path may be defined by guides of various designs sufficient to hold and guide the lens cover film along the pre-set travel path. The guide may include rails or slits through which the lens cover film passes. The guide is generally constructed as an integral part of the body of the device (6). The guide(s) and body of the device are further described in the detailed description.

In one embodiment, the flexible lens cover film (3) is retained on a first spool, unwound and captured on a second spool such that any particular section of the lens cover film passes in front of the objective lens only once. Having become soiled, the lens cover film is incrementally wound onto the second spool and a clean section of lens cover film moves into place in front of the objective lens. In an alternative embodiment, a section of the flexible lens cover film (3) may be moved alternately bi-directionally (i.e., back and forth) in front of the objective lens (or lens cover, if present). Movement of the lens cover film through the guide slits (7 and 8) will cause a section of the lens cover film to be cleaned, and this section will then be moved back in front of the objective lens. In one embodiment the guide slits (7 and 8) may be edged with flexible wiper blades, made of, for example, silicone, rubber or plastic. As the lens cover film passes between the wiper blades, solid and liquid debris is removed, and the cleaned section of film may them be repositioned in front of the objective lens. This embodiment is advantageous because it requires the use of a shorter length of lens cover film and it requires less complex apparatus to retain the film.

The spools from and onto which the lens cover film is wound may be manipulated manually via dials mounted at the proximal end of the device. The dials may be positioned in any suitable disposition (for example see the control dials on a standard fiber-optic gastroscope). The spools may incorporate a spring biasing means (on the first spool) and a ratcheting means (on the second spool) such that the lens cover film is kept taut and can only be moved along the transit path in one direction. The control dials may incorporate gearing means by which the lens cover film may be drawn through the transit path at a slower or faster speed. The control of the movement of the spool or spools may be achieved via any means mechanically in some embodiments or electrically in other embodiments.

In certain embodiments the device is designed to have disposable elements or to be entirely disposable. Disposability is really a function of cost in relation to expense of sterilization. Heat and chemical sterilization is a relatively inexpensive process, but it may damage certain or the more delicate elements of an apparatus. For example, the lens cover film, depending on the material from which it is made, may be clouded or otherwise damaged by heat and oxidative agents (bleach). The lens cover film may be made from any transparent material such as polythene, acetate polyvinylchloride or other polymers which are inexpensive and may be disposable. The lens cover film may be made from any transparent material that has high melting temperature and can withstand the heat generated at the endoscope objective lens (2). In certain embodiments, the lens cover film may be augmented, coated, or treated with any additional component (of any means such as chemical or electrical) to achieve anti-fog capability. Surfactant, polymer, or corona treatment, for example, may provide a hydrophilic surface to the lens cover film that can provide anti-fog quality to the film. In other embodiments, the entire device may be disposable, dispensing with the need for sterilization altogether.

The body of the device is essentially a tube and may be made of any material (or any combination of materials) such as metal or molded plastic, for example polymers such as PTFE, polyvinylchloride, polypropylene, polyethylene, polyester or polyamide. Alternatively the body of the device may be in the form of a flexible sheath made at least partially from a material that will snuggly fit over and conform to the shape of the endoscope. Such materials include latex, rubber and woven elastic fabrics. The device may include a lens cover (22) at the distal tip, which may be made of any transparent material such as an acetate polymer and is able to withstand the heat generated at the objective lens (2) without melting or change.

The surface of the lens cover film (3) may be made parallel to the surface of the objective lens (2) via any means, such as the use of support frames (23, 24), scaffolds, or specific device body distal tip design. The support frames, scaffolds, or distal device body tip may be made of any dimension, configuration, or material, such as nitinol, that may or may not have flexibility, inherent memory or elastic properties.

The present invention encompasses a number of different embodiments all of which remove debris and dirt from the viewing path of an endoscope. Some of these embodiments utilize a lens cover film that moves through a pre-set travel path, while others use various mechanical means to keep the viewing path and objective lens free of obstructive matter.

An alternate variation of the device of the invention employs a transparent lens cover coated with a coating that inherently repels fluids and other contaminants. Such a coating could, for example comprise a highly hydrophobic material such as polysiloxanes, fluoride compounds and a silane compounds. Such coatings are commercially available. Coatings can also be made so that they hold very little electrostatic charge and so that they form a very smooth molecular surface. All these qualities make a coated surface repellant to fluid and dirt. Such a coated lens cover could be employed alone or on combination with the other various embodiments of the invention.

The device of the invention may additionally incorporate various functional elements such as light sources, vacuum means, gas and liquid conduits, instrument conduits, biopsy instruments and various instruments used to help visualize a target or perform surgical procedures. For example, one or more light sources may be set into the distal end of the body of the device to provide illumination of a target. Such light sources may be provided by one or more electric lamps (incandescent or LED) mounted at the distal end of the device or the light may be transmitted via fiber optic conduits from a remote light source to the tip of the device. A remote light source may be provided separately from the device and may be coupled to the fiber optic cables by standard couplings. In another example, the body of the device may incorporate one or more vacuum conduits that may be used to produce suction at the distal tip of the device by which fluids such as blood and other body fluids may be removed. Such devices are well known in the art. Other alternate embodiments may employ conduits within the body of the device through which a gas can be pumped; for example, air or an inert or non-reactive gas is commonly pumped into the body cavity during procedures to enhance visualization, e.g. carbon dioxide, nitrogen, etc. Conduits may also transmit fluids such as sterile water and saline that may be used to wash and clean areas to be viewed. Such liquid may be removed via the suction tube. Other conduits may be used to deliver drugs such as local anesthetics and therapeutics. Additionally, a laser conduit may be employed to transmit laser light to a target, for example for ablation and cauterization of tissue. As mentioned above, other embodiments may include instruments such as biopsy needles and cutting instruments that may be operated remotely by the user from the proximal end of the endoscope.

The device of the invention may be fixed to the endoscope by any standard means. For example a luer-lock, strap, latch, pin or screw mechanism may be used to removeably clip the endoscope into the lumen of the invention and maintain the relative position of the endoscope and the device while in use.

The device of the invention may be used for endoscope of different objective lens orientation (such as 0 degree, 15 degree, 30 degree, 45 degree, 60 degree, and 70 degree endoscopes). Frames (flexible or rigid, of any material or design), scaffolds (flexible or rigid, of any material or design), or distal device tip design may be used to allow the surface of lens cover film (3) become parallel to the surface of objective lens (2), thereby allowing viewing without light deflection or image distortion.

The device of the invention may include transparent lens cover (22) integrated as part of the device body (6), thereby separating the device body lumen from device exterior surface. This would allow the use of endoscope (1) accommodated within the device body lumen without the need for sterilization of the endoscope, as the endoscope has no direct physical contact with body tissues. Additional slits or channels of various design or dimensions may be built within the device body to allow passage of air, fluids, debris, and/or endoscopic instruments. In fact, these additional slits or channels may be proximally associated with buttons, dials, openings, controls, or other designs and means and may be connected to vacuum source (for suction to remove debris from body cavity), air source (for pumping air into body cavity), or fluid irrigation source (for irrigation into body cavity). These features are particularly useful if the endoscope involved is a colonoscope, gastroscope, bronchoscope, and laryngoscope.

Although the examples in this disclosure concentrate upon embodiments where the device is separate from an endoscope and wherein the endoscope is placed within the lumen of the device, this invention additionally encompasses embodiments where the device to keep the objective lens free of debris is incorporated into the structure of an endoscope. In its most basic embodiment the integrated endoscope embodiment comprises an endoscope having lens cover film and a means for guiding the lens cover film in front of the objective lens. Such embodiments may employ any or all the features of the separate embodiments.

In use, an endoscope, for example a laparoscope, is placed within the lumen of the body of the device of the invention. The objective lens of the laparoscope abuts or is in close proximity to the distal end of the tube. The distal end of the tube may be open or may terminate with a transparent window or lens cover. The entire device may be inserted into and through a standard laparoscopic trocar or a specially designed trocar. Via the trocar, the laparoscope can be placed inside the body cavity. During use the lens cover film may be moved in a preset travel path in front of the endoscope objective lens (and the lens cover, if present). The lens cover film may travel unidirectionally or bidirectionally. Any particular section may be used only once, or may be cleaned, for example by fixed wiper blades present at the guide slits, and reused by reversing the travel path of the lens cover film.

The shape and size of the current invention may be selected for fitness for any specific purpose. For example, the present device may be used for any of the existing laparoscopes available in the market (such as 10 mm, 5 mm, 2 mm scopes) and may be used in conjunction with any of the existing laparoscopic trocars. Alternatively the invention may be used with specially designed laparoscopic trocars specifically designed to work with the present invention. For example, the body of the device may have a diameter of from 3 mm to 25 mm, or for example about 3 mm, 7 mm, 12 mm, 25 mm, 18 mm or 22 mm. The length of the device may be any length compatible with its function of maintaining a clear optical/visual pathway, and the device may (or may not) be shorter than the endoscope that is inserted into it. For example, the device may be from 4 cm to 30 cm in length, or for example about 5 cm, 7 cm, 10 cm, 14 cm or 18 cm in length. The body of the invention may be of variable fixed lengths, or it may be of dynamically adjustable length by use of a telescoping designs. The body of the invention is generally an elongated cylinder, though it may be of any suitable cross-sectional shape such as oval, triangular, square, polygonal, or polymorphous. The body of the invention may be rigid or may be flexible. A flexible body is desirable when using a flexible endoscope. The body of the device may be made from any biocompatible material, such as polyvinylchloride (PVC), polystyrene, polytetrafluoroethylene (PTFE), polypropylene, polyethylene, polyester or polyamide or other plastics or acrylics or rubber, or may be made of a metal such as a nickel-titanium alloy of stainless steel etc. The body of the device may be made from various manufacturing process(es) including heat shrinkage process. The lens cover film may be made from any transparent material such as polythene, polypropylene, polyacetates, polyvinylchloride or any other polymer materials. The lens cover film support scaffolds or frames (23 and 24) may be made from any material such as nitinol that may have memory or intrinsic elastic properties.

The present invention provides various advantages over the prior art devices and methods. The present invention provides devices that maintain a clear and unobstructed view through the objective lens of an endoscope while in use; devices that clear obstructive fluids and debris from the optical path of an endoscope while in use, devices that eliminate the need for the endoscope to be withdrawn from the patient on order that the objective lens may be cleaned, and devices that eliminate the need for endoscope sterilization during its use. This advantage of eliminating the need for endoscope withdrawal and objective lens cleaning is particularly important as removal and reinsertion of an endoscope slows surgical procedures, increases trauma, and can significantly impact surgical outcomes. Additionally, the present invention is simple and inexpensive to manufacture, simple to use and robust in use, and can be used with a variety of endoscopic devices.

In one aspect, endcap (30) may be configured to reduce or eliminate fluid infiltration between the lens cover film (3) and the lens (2), which might otherwise result from factors such as capillary action at the film edges. As one of skill in the art will appreciate, once between the film and lens, bodily fluid would become difficult to clean off from the lens and likely remain trapped in between film and the lens, degrading performance. As described above, the proximal portion (31) and distal portion (32) of endcap (30) may sandwich lens cover film (3) to seal the edges of the film, to holds the film flat, and/or to keep the film in alignment as it traverses pass the lens surface. Thus, when the portion of lens cover film (3) in front of the viewing field of endoscope (1) is exposed to the abdominal environment or other body cavity, contaminant such as fluid or debris may soil the distal surface and reduce viewing clarity. By advancing lens cover film (3), the viewing field may be cleared. The endcap (30) may reduce or prevent fluid infiltration issue by sealing the edges of the film as it is moved along its travel path.

The proximal portion (31) may be designed to allow film passage from device body (6) into endcap (30), such as through outside edge cut-out, slits, or sizing configurations relative to the distal portion (32). Lens cover film (3) may be at least wider than the opening (34) of the distal portion (32)

so that the film edges are covered by the distal portion (32) and, in some embodiments sandwiched between the distal and proximal portions.

Accordingly, device body (6) may be single or multi-lumen and may be connected to endcap (30) by mechanical interlock, adhesive or other suitable means. In some embodiments, multiple lumens may be used to protect the lens cover film (3) from being soiled by separating the clean film portion from the dirty film, as well as by separating the film from the endoscope (1).

In another aspect, the configuration of the endcap (30) may employ openings and/or windows on the proximal (31) and distal (32) portions of varying shapes and sizes that may also vary between the distal and proximal portions. For example, in some embodiments, the proximal portion (31) has a circular opening (33) while the distal portion (32) has a rectangular opening (34) to cover the film's side edges along its travel path. Generally, a main opening at least as large as the viewing field may be used. The distal portion (32) may cover the film delivery section to help protect the clean film from becoming soiled before moving to cover the viewing field and thus ensure clean film can be delivered. Opening (34) of the distal portion (32) may have straight edges along the film's travel path to help facilitate fluid movement away from the viewing field. As noted, opening (34) may have a cut-out extending below the viewing field to form a horseshoe configuration or may employ channels (40) to facilitate clearing of debris and fluid. Fluid and/or debris may be transported by the moving film to the bottom edge of the device without reduced obstruction. Furthermore, movement of the film provides momentum so that contaminants may more easily be transported off the edge of the device.

The proximal (31) and distal (32) portions may be of different thickness and rigidity. Similarly, the endcap (30) may be rigid, semi-rigid, or flexible. In one embodiment, distal portion (32) may be relatively rigid and proximal portion (31) may be relatively flexible, functioning as a washer. Alternatively, the distal portion (32) may be relatively more flexible than the proximal portion (31). Further, end cap (30) may be transparent, translucent or opaque as desired, so long as the viewing field remains clear. As such, the proximal (31) and distal (32) portions may have different transparency levels. Endcap (3) may be made of any suitable material, such as polycarbonate, acrylic, boPET, rubber or other polymers. Materials with hydrophobic properties may also be used as desired. The proximal (31) and distal (32) portions may be one integrated piece, assembled to be interconnected, or assembled to be in contact. Thus, in some embodiments, the endcap (30) may be assembled together from two separate proximal (31) and distal (32) portions, such as with adhesive or mechanical interconnection.

As one example, the distal portion (32) may be made from polycarbonate, acrylic, or other highly transparent material. The proximal portion (31) may be made of a layer film (e.g., boPET) that has high optical clarity. In one aspect, the proximal portion (31) is placed between the lens of the viewing instrument and the film and may be relatively thin to minimize the gap between the lens and the film. This characteristic may be balanced against a desirable structural integrity to support the film. In one exemplary embodiment, a boPET proximal washer with thickness of 0.05" is used in conjunction with the portion (32) to sandwich the film and provide adequate sandwich seal.

Further, the proximal (31) and distal (32) portions of endcap (30) may be configured to minimize infringement of the viewing field of the endoscope (1). For example, openings (33) and (34) may be sized to avoid covering the viewing field. For a 10 mm laparoscope, the openings may be as small as 0.180" depending on the thickness of the endcap (30). With an endcap (30) having a thickness of approximately 0.030", the openings may be approximately 0.200"-0.22" to maintain the viewing field. In other embodiments, openings of 0.220"~0.300" may also be employed.

The lens cover film (3) may have a width greater than opening (34) as noted. In one aspect, an effective sandwich seal on the film's edges may be obtained with an overlap of approximately at least 0.010". The lens cover film (3) may be placed so that it is essentially centered in the endcap (30) and both film edges may be sufficiently sealed. Thus, film approximately at least 0.020" wider or greater may be used in some embodiments. Although film of sufficient width to provide a seal is desired, travel path and overall device size may constrain the film width to allow a relatively flat configuration in the travel path, thereby avoiding wrinkling issues that may occur when making sharp turns to traverse across the lens surface.

Sufficient compressive force may be applied between the proximal (31) and distal (32) portions to help enhance the sandwich seal without impeding film movement. Even pressure along the sealing edges may be employed to enhance sealing effectiveness.

The present disclosure also provides the advantage of increasing the degree to which the lens cover film (3) is kept flat and/or perpendicular to the lens (2) when traversing across the viewing field to maintain optical clarity and minimize image distortion. Furthermore, these designs reduce any creasing, wrinkling, or imperfection imparted to lens cover film (3), which would otherwise negatively impact image quality. Since the overall size of the trocar used to gain access to the patient limits the space available for the device body (6), delivery and retraction of the film may involve a sharp turn (such as about 90 degrees for a 0 degree laparoscope) to traverse in front of the lens (2). Thus, in some embodiments, the film transitions from "arc to flat" occurring at delivery onto the viewing field and transition from "flat to arc" occurring when film exits from viewing field. The designs of this disclosure minimize wrinkling of the film under these conditions.

For example, one or more lumens in device body (6) that carry lens cover film (3) may be configured to keep the film in alignment as it travels into and out of the endcap (30). In some embodiments, the device body (6) lumen may not be concentric. In other variations, device body (6) may have flat inner walls on opposite side of the lumen accommodating the viewing instrument. Similarly, any guiding elements (e.g., 7, 8, 36, 37, 38, 39, 52, 53, 61, 62, 65 and 66) accommodating the lens cover film may be of any dimension and design (linear, curvilinear, arc-like, or others) at specific cross sections the device and may vary. In some embodiments, as described herein, the guide elements feature a straight edge to facilitate travel of lens cover film (3) without wrinkling. In one aspect, the lumens may have a semi-circular configuration with flat sections (such as lumens 38 and 39) that run the length of device body (6). Alternatively, the lumen profile may change, such as from a concentric lumen to non-concentric flatter lumen to flat-walled lumen. The walls engaging the film become flatter towards the distal end. The lumen profile gradient allows the film to transition from a circular arc to an arc with less curvature and to flat where the film makes a sharp turn. In some embodiments, the diameter of device body (6) may vary, such as shown in FIGS. 15A and 15B, to accommodate such transitions.

The straight edges of the guiding elements may facilitate the transitions between arc and flat, by providing a flat edge rather than a single contact point on circular lumen wall. Such designs may include two inner flat-walls (straight-edges or flat-sides) positioned on opposite-side to provide flat film travel path and to enable film turning over flat edge. Further, the straight edge may have a smooth profile to further reduce potential wrinkling of the film. In other embodiments, flattened sections of device body (6) may help guide the film and allow the film to travel in "substantially" flat rather than in arc conformation. In contrast, conventional designs may have a single contact point formed by the circular inner lumen that may cause film to wrinkle in the center area, which is the area that travels in front the lens and covers the viewing field.

A device body (6) having lumens with straight edges may be one integrated piece or may be assembled together using coaxial portions. Lens cover film (3) may be positioned over the inner portion and an outer tube may be disposed over both. A two piece device body (6) may be assembled by mechanical interlocking parts, adhesives or other suitable means.

The width of any flat sectioned lumen of device body (6) may be limited by the trocar opening diameter, endoscope (1) diameter and sheath wall thickness. In some embodiments, the film travels completely flat and may be sized to approximate the width of the inner flat sections. In other embodiments, the film may be slightly wider, traveling in the lumen with some arc configuration and then transitioning to a flat configuration at the straight edges when turning. In some embodiments, a degree of wrinkling at the edges may be permissible when the center section is maintained relatively wrinkle-free.

The present disclosure also includes designs that may improve the effectiveness of sealing with endcap (30). For example, the edges of lens cover film (3) may be configured to reduce capillary action of otherwise optimize the seal with the proximal portion (31) and the distal portion (32). The edges may also facilitate holding lens cover film (3) flat within the viewing field. The sliding film's edges may have increased thickness or may take on different pre-shaped formations to create better sealing effect and maintain optical clarity when sandwiched by the endcap (30). In one embodiment, the relatively thicker film edges act as a retaining wall for fluid. The center portion of the film may be flat and thin to provide for high optical clarity. The thicker edges may be add-on pieces to increase height via secondary processing (e.g., adhesive, etc.), co-extrusion, by rolling the edges to create one or more layers or in any other suitable manner. In another embodiment, the edges of the film may be pre-shaped into primarily upward configuration while the center portion of the film is flat to provide for optical clarity. The pre-shaped film or thick-edged film may travel through the lumen of the device body (6) and slide into the endcap (30) with corresponding slots (grooves) for the shaped film edges to slide-n-lock into place, improving the seal and stability of the film in the viewing field. The film may form a channel to transport fluid more effectively. When the film is transported, fluid moves off the viewing field cleanly and quickly, while little or no gap is provided for capillary action to occur.

Another feature is disclosed to improve the effectiveness of sealing with endcap (30). On backside of the distal portion (32) around the edges of opening, sealing pad (72) may be configured to avoid fluid or blood infiltration between proximal portion and distal portion. Sealing pad (72) can be squeezed or compressed slightly to form a thin barrier between proximal portion and distal portion to block infiltration.

Although the various exemplary embodiments of the present invention are directed to medical endoscopic uses, the present invention is not limited to such uses, and the device described may be used for any application in which it is important to maintain a clear optical path through the lens of a viewing instrument. The device can work equally with any type of viewing instrument or illuminating instrument to maintain a clear and unobstructed optical path. Such instruments may be used to visualize a target or to illuminate a target or both. The invention serves just as well to maintain a clear path for a beam of outgoing light as for a viewing lens. Alternative embodiments and applications include applications for sewer and drain cameras, which come in all manner of different formats. Some are similar to hand-held fiber-optic gastroscopes and can be inserted down a drain and through pipes. Others are large robotic instruments mounted on remote controlled power-trains that can be sent far along sewer pipes. Similar instruments are used to inspect gas and oil pipelines. In all these applications fouling of the optical pathway is a common and serious problem.

Other applications of the current device may include providing unobstructed view to (1) lenses or cameras mounted on military vehicles or other motor vehicles such as race cars and (2) lenses or cameras used for wildlife filming or viewing. In such applications, the fouling of lenses and optical pathways by dust, fluids such as rain and mud are well known problems. Yet other embodiments include the use of the present invention to maintain a clear optical path for a photovoltaic device. The efficiency of such instruments, for example the conversion of solar energy into electrical energy by a solar panel, can be significantly diminished if small or microparticulate dust accumulates on the surface of the solar cells. This is particularly a problem encountered with the solar panels on the Mars rovers Opportunity and Spirit. Maintaining elevated levels of electrical output to the rover's storage batteries from such panels can significantly extend the useful life of the rover in such an extra-terrestrial mission. The device of the invention solves such problems in the same way as described above for the endoscopy examples. In the case of a viewing apparatus, the embodiment may involve the tubular system using a lens cover film that provides a continuously clear transparent covering for the lens or a camera and/or lamp. The lens cover film may be operated manually, electrically, robotically, or via other means. In other embodiments brushes and coated lenses may be used as described above.

It will be readily appreciated that various adaptations and modifications of the described embodiments can be configured without departing from the scope and spirit of the invention and the above description is intended to be illustrative, and not restrictive, and it is understood that the applicant claims the full scope of any claims and all equivalents.

What is claimed is:

1. A device for maintaining a clear optical path comprising:
   an elongated hollow body comprising a proximal end and a distal end, wherein the elongated hollow body defines a lumen adapted to receive a viewing apparatus having a lens;
   a transparent lens cover film movably associated with the elongated hollow body so as to describe a preset travel path passing in front of the lens of the viewing apparatus, wherein the lens cover film comprises first and second opposing surfaces; and an endcap configured to engage opposing edges of the lens cover film in a sealing manner, the end cap including: i) a distal portion having an opening that aligns with the lens of the viewing apparatus and an inner surface adjacent the opening that engages at least a portion of the first surface of the lens cover film, and ii) a proximal portion having an opening that aligns with the lens of the viewing apparatus and an outer surface adjacent the opening that engages at least a portion of the second surface of the lens cover film, such that the lens cover film is positioned between the distal portion and the proximal portion, with the first surface of the lens cover film engaged by the distal portion and the second surface of the lens cover film engaged by the proximal portion, wherein the second surface of the lens cover film is engaged around a perimeter defined by the opening of the proximal portion.

2. The device of claim 1, wherein the proximal portion further comprises two parallel guides through which the lens cover film passes.

3. The device of claim 1, wherein the proximal portion further comprises an optical path.

4. The device of claim 1, wherein at least one edge of the opening of the distal portion comprises a fluid travel path.

5. The device of claim 4, wherein the fluid travel path comprises a cut-out in the distal portion.

6. The device of claim 4, wherein the fluid travel path comprises at least one channel formed in the distal portion.

7. The device of claim 1 wherein the lumen of the device is adapted to receive an endoscope or laparoscope.

8. An apparatus for maintaining an optical property comprising:

an optical apparatus;

a movable member containing a first portion and a second portion; wherein the movable member comprises first and second opposing surfaces; wherein the first portion overlaps at least part of the optical apparatus; wherein the first portion is replaceable with the second portion, so that an optical property is retained when at least part of the first portion is replaced with at least part of the second portion; and an endcap configured to engage opposing edges of the movable member in a sealing manner, the end cap including: i) a distal portion having an opening that aligns with the lens of the optical apparatus and an inner surface adjacent the opening that engages at least a portion of the first surface of the movable member, and ii) a proximal portion having an opening that aligns with the lens of the viewing apparatus and an outer surface adjacent the opening that engages at least a portion of the second surface of the moveable member such that the movable member is positioned between the distal portion and the proximal portion, with the first surface of the movable member engaged by the distal portion and the second surface of the movable member engaged by the proximal portion, wherein the second surface of the moveable member is engaged around a perimeter defined by the opening of the proximal portion.

\* \* \* \* \*